(12) United States Patent
Zou et al.

(10) Patent No.: US 9,988,609 B2
(45) Date of Patent: Jun. 5, 2018

(54) FRUCTOSE AMINO ACID OXIDASE, PREPARATION METHOD AND ENZYME-CONTAINING KIT FOR DETECTING GLYCATED ALBUMIN

(71) Applicant: NINGBO MEDICAL SYSTEM BIOTECHNOLOGY CO., LTD., Ningbo (CN)

(72) Inventors: Bingde Zou, Ningbo (CN); Jihua Zou, Ningbo (CN); Yi Wang, Ningbo (CN); Jianghua Jia, Ningbo (CN)

(73) Assignee: MEDICAL SYSTEM BIOTECHNOLOGY CO., LTD., Ningbo (CN)

( * ) Notice: Subject to any disclaimer, the term of this patent is extended or adjusted under 35 U.S.C. 154(b) by 0 days. days.

(21) Appl. No.: 15/108,320

(22) PCT Filed: Dec. 11, 2014

(86) PCT No.: PCT/CN2014/093580
§ 371 (c)(1),
(2) Date: Jun. 27, 2016

(87) PCT Pub. No.: WO2015/096621
PCT Pub. Date: Jul. 2, 2015

(65) Prior Publication Data
US 2016/0319248 A1   Nov. 3, 2016

(30) Foreign Application Priority Data
Dec. 27, 2013  (CN) .......................... 2013 1 0744635

(51) Int. Cl.
*C12Q 1/26* (2006.01)
*C12N 9/62* (2006.01)
*C12N 9/06* (2006.01)
*G01N 33/68* (2006.01)

(52) U.S. Cl.
CPC .......... *C12N 9/0032* (2013.01); *C12Y 105/03* (2013.01); *G01N 33/6842* (2013.01); *G01N 2333/765* (2013.01); *G01N 2333/90638* (2013.01); *G01N 2333/90672* (2013.01)

(58) Field of Classification Search
None
See application file for complete search history.

(56) References Cited

U.S. PATENT DOCUMENTS

| 5,948,659 | A * | 9/1999 | Kato ..................... C12N 9/0022 435/189 |
| 7,091,017 | B2 * | 8/2006 | Sakaue ................. C12N 9/0022 435/190 |
| 8,497,083 | B2 * | 7/2013 | Ikebukuro ............ C12N 9/0022 204/403.14 |
| 9,701,949 | B2 * | 7/2017 | Masakari ............. C12Y 105/03 |
| 2012/0208226 | A1 * | 8/2012 | Ikebukuro ............ C12N 9/0022 435/25 |

FOREIGN PATENT DOCUMENTS

| CN | 102559643 A | 7/2012 |
| CN | 103695380 A | 4/2014 |
| JP | 2004275013 A | 10/2004 |
| WO | WO2002061119 A1 | 8/2002 |
| WO | WO2006013921 A1 | 2/2006 |
| WO | WO2007049762 A1 | 5/2007 |

OTHER PUBLICATIONS

Sakaue et al., Appl. Environ. Microbiol., 69(1):139-145 (2003).*
Ferri et al, J. Diabetes Sci. Techol., 3(3):585-592 (2009).*
Lin, Z. and J. Zheng(2010). "Occurence, characteristics, and applications of fructosyl amine oxidases (amadoriases)." Appl Microbiol Biotechnol 88(6): 1613-1619.
Yoshida, N., Y. Sakai, et al, (1996). "Primary structures of fungal fructosyl amino acid oxidases and their appliation to the measurement of glycated proteins," European Journal of Biochemistry 242(3): 499-505.
Sakai, Y., N. Yoshida, et al. (1995), "Purification and properties of fructosyl lysine oxidase from Fusarium oxysporum S-1F4." Bioscience, biotechnology, and biochemistry 59 (3): 487.
Mennella, C., R. C. Borrelli, et al. (2005). "Substrate specificity of amadoriase I from Aspergillus fumigatus." Ann N Y Acad Sci 1043: 837-844.
Sakaue, R. and N. Kajiyama(2003). "Thermostabilization of bacterial fructosyl-amino acid oxidase by directed evolution." Applied and environmental microbiology 69(1): 139-145.
Hirokawa, K., A., Ichiyanagi, et al. (2008). "Enhancement of thermostability of fungal deglycating enzymes by directed evolution," Appl Microbiol Biotechnol 78(5): 775-781.
Miyazaki, K. (2003). Creating random mutagenesis libraries by megaprimer PCR, of whole plasmid (MEGAWHOP). Directed Evolution: Library Creation, Springer: 23-28.
GenBank: AAB88209.1 "Fructosyl amine: oxygen oxidoreductase [Aspergillus fumigatus]".

\* cited by examiner

*Primary Examiner* — Thomas J. Visone
(74) *Attorney, Agent, or Firm* — Gokalp Bayramoglu

(57) ABSTRACT

Fructosyl amino acid oxidase is provided, which has an amino acid sequence as shown in SEQID. No. 1 or fructosyl amino acid oxidase having a homology of more than 80% with this amino acid sequence, on a corresponding site of an amino acid selected from following (a) to (f), having one or more amino acid residues conducting a substitution, obtained fructosyl amino acid oxidase having a higher thermostability: (a) 59-site glutamic acid, (b) 98-site glutamic acid, (c) 225-site glycine, (d) 277-site lysine, (e) 285-site glutamic acid, and (f) 355-site aspartic acid. The method for preparing the above oxidase and the test kit containing the enzyme for determining glycated albumin are also provided.

8 Claims, 2 Drawing Sheets

FRUCTOSE AMINO ACID OXIDASE, PREPARATION METHOD AND ENZYME-CONTAINING KIT FOR DETECTING GLYCATED ALBUMIN

TECHNICAL FIELD

The present invention relates to the field of in vitro diagnostics, in particular, a fructose lysine oxidase mutant with a high thermostability, a method for determining levels of glycated albumin, and a test kit for determining the glycated albumin levels. The present invention can be used in clinical testing, and can accurately determine glycated albumin levels.

BACKGROUND

Diabetes is a metabolic disease occurring in people with high blood sugar, and can lead to serious damage to many systems of the body, especially the nerves and blood vessels. According to the expectation of the World Health Organization, the number of people with diabetes in China has been ranked first in the world. Diabetes will be the most serious public health problem in China in the next 50 years.

Glycated albumin (GA) is the product formed by a non-enzymatic reaction occurring between glucose and glycated N-terminus albumin in human serum. 90% of them reacts with albumin within the chain of lysine ε-NH2 residue. The reaction principle lies in, at first both of them form an unstable Glycosylamine or Schiff Base. Then, through irreversible Amadori rearrangement, the latter forms a stable amino ketone (ketone amine). Since the half-life of albumin is about 20 days, detection of glycated albumin can be used to detect the average level of blood sugar over the past 2-3 weeks. Currently, glycated albumin testing has become an essential test for diabetics. Compared with glycated hemoglobin, it is more suitable as an index for assessing the risk of hospitalization and death of diabetic patients who have had dialysis.

Therefore, how to accurately determine the amount of glycated albumin in human's serum has become the key of clinical detection of glycated albumin. Currently, the market mainly uses enzymatic method to detect glycated albumin in human's serum. The reaction principle lies in, using protease at first, glycated albumin is digested into glycated polypeptides with a low molecular weight. Then, using fructosyl amino acid oxidase to catalyze glycated polypeptides to perform the oxidation reaction to generate polypeptides (or amino acids), Arabino hexose and $H_2O_2$. Release of $H_2O_2$ is detected by an endpoint reaction colorimetric method. Absorbance at 600 nm is proportional to the concentration of glycated albumin. Specific reaction process is as follows:

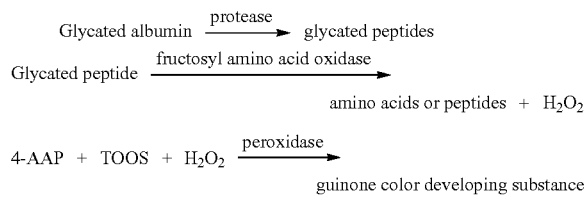

As is known form the above reaction mechanism and reaction steps, fructosyl amino acid oxidase is the key enzyme of detecting glycated albumin, and fructosyl amino acid oxidase has become the key for whether glycated albumin in human's serum can be accurately detected.

Fructosyl amino acid oxidase can also be referred as Fructosyl amino acid enzyme. Amadoriase, ketone oxidase, and etc. Such fructosyl amino acid oxidase has already been found in many bacteria, yeasts, and fungi, for example, from *Aspergillus, Penicillium, Fusarium, Pichia, Coniochaeta, Eupencillum, Corynebacterium*, and etc. (non-patent document 1, Lin, Z. and J. Zheng (2010) "Occurrence, characteristics, and applications of fructosyl amine oxidases (amadoriases)." Appl Microbiol Biotechnol 86. (6): 1613-1619). The above fructosyl amino acid oxidases are all possible to be applied in the glycated albumin test kit. However, at the same time, since in practice the diagnostic test kit need to be stored for a certain period of time, the requirements for stability are relatively high. Thus, the raw material-enzymes used also need to be stable. However, the thermostability of the enzymes shown in the above public materials are not ideal. After a heating treatment at 45° C. for 10 minutes, fructosyl amino acid oxidase from *Aspergillus terreus* GP1 shows a residual enzyme activity of about 40% (Non-Patent Document 2: Yoshida, N., Y. Sakai, et al (1996) ". Primary structures of fungal fructosyl amino acid oxidases and their application to the measurement of glycated proteins" European Journal of Biochemistry 242 (3): 499-505). After a heating treatment at 45° C. for 5 minutes, fructosyl amino acid oxidase from *Fusarium oxysporum* S-1F4 shows a residual enzyme activity of about 10% (Non-Patent Document 3: Sakai, Y., N. Yoshida, et al (1995). "Purification and properties of fructosyl lysine oxidase from *Fusarium oxysporum* S-1F4" Bioscience, biotechnology, and biochemistry 59 (3): 487). After a heating treatment at 37° C. for 30 minutes, fructosyl amino acid oxidase from the *Coniochaetidium savoryi* ATCC36547 shows a residual enzyme activity of 80% (Japanese Patent Application Publication No. 2004-275013;). Because of the poor thermostabilities of existing fructosyl amino acid oxidases, the stability of glycated albumin test kits on the market nowadays cannot meet the requirements. In many cases, a large amount of stabilizer is added in the test kit, so as to increase the stability of the test kit (International Patent Application Publication No. WO02002061119A1). This leads to a higher viscosity of the reagent, as well as a series of other issues. It is not conducive to be applied in a biochemical analyzer.

Therefore, there is an urgent need to develop a fructosyl amino acid oxidase with high thermostability. Also, this fructosyl amino acid oxidase is used to develop a glycated albumin test kit having both high sensitivity and long-term stability.

SUMMARY

For the above-mentioned deficiencies of the prior art, the present invention provides a fructosyl amino acid oxidase having a high thermostability.

Amadoriase I (its amino acid sequence is the sequence shown in sequence 1, i.e., SEQID. No. 1: its nucleotide sequence is sequence 2, i.e., the sequence shown in SEQID. No. 2) from *Aspergillus fumigatus* has the characteristic that the activity for a substrate fructose lysine is far greater than that of fructosyl valine (non-patent document 4: Mennella, C., R C Borrelli, et al (2005) "Substrate specificity of Amadoriase I from *Aspergillus fumigatus*." Ann NYA cad Sci 1043: 837-844.). Such a characteristic makes it particularly suitable for the glycated albumin test kit. The glycosylation site of glycated albumin is a lysine residue, which is different from a valine residue of glycated hemoglobin.

This helps to reduce interference in other factors in the test. Therefore, from this point, the enzyme is modified to improve its thermostability. The sequence of Amadorise I has a very low homology with sequences of FAOX-TE and FPOX-CE as previously reported (Non-Patent Document 5: Sakaue, R. and N. Kajiyama (2003) "Thermo stabilization of bacterial fructosyl-amino acid oxidase by directed evolution "Applied and environmental microbiology 69 (1): 139-145 Non-Patent document 6: Hirokawa, K., A. Ichiyanagi, et al (2008)". Enhancement of thermos stability of fungalde glycating enzymes by directed evolution "Appl Microbiol Biotechnol 78 (5): 775-781). Therefore, it is impossible to obtain relevant information simply by the sequence comparison. However, information about the transformation of the enzyme must be obtained through a lot of creative research.

Specifically, the random mutating method is utilized, to increase the thermostability of Amadorise I. The method is as follows:

(1) Using the gene sequence of fructosyl amino acid oxidase of Amadorise I as a template, error-prone PCR amplification is conducted, to establish mutagenesis libraries of fructosyl amino acid oxidases.

(2) The mutagenesis libraries are transferred into Escherichia coli. It is cultivated using 96-well plate and induced to express.

(3) Bacteria are lysed on site. Activity is measured using a quinone method. The fructose lysine oxidase with high thermostability is selected.

In the present invention, using the nucleotide sequence 2 as a template, designing primer sequence 3 (5'-atggcgcct-tcaattttgagcactg-3') and primer sequence 4 (5'-ttacggacctct-gctctctccaatc-3'), error-prone PCR is conducted. By reasonably controlling the concentration of manganese ions in a PCR reaction system, the mutagenesis frequency is controlled to 1 to 2 nucleotide mutageneses/1 Kb nucleotides. After the obtained fragment containing the mutant nucleotide is purified, using pET-22b plasmid containing the nucleotide sequence 2 as a template, the whole plasmid PCR (WHOP-PCR) is conducted (non-Patent Document 7: Miyazaki, K. (2003) Creating random mutagenesis libraries by mega primer PCR of whole plasmid (MEGAWHOP) Directed Evolution Library Creation, Springer: 23-28). The obtained product is enzyme digested using the restriction enzyme DpnI, so as to remove the template plasmid. Thereafter, TOP10 competent cells were transformed, and are applied to LB agar plate containing antibiotic ampicillin. The obtained clones are approximately 10,000. Therefore, the library capacity of the random mutagenesis is about 10,000.

After the obtained clones are mixed well with a coating bar, they are collected in the centrifuge tube. The plasmid is extracted. The obtained plasmid is transformed into BL21 (ED3), so as to be ready for use in the next step of screening Subsequently, the transformant is inoculated in a 96-well plate. The cultivation medium is 150 ul LB/per well, containing the antibiotic ampicillin. This plate is used as a retention plate. The next day, in the same order, it is transferred to another 96-well plate. The cultivation medium is 150 ul LB/per well. Meanwhile, the antibiotics ampicillin and IPTG are added for induction. It is cultivated for 6 hours at 37° C. Bacteria are harvested by a centrifugation of 3800 rpm. The medium is removed. The plate is used as the assay plate.

150 ul of lysis solution (100 mM Tris, pH 8.0; 0.4 mg/ml sodium deoxycholate; 0.8 mg/ml CTAB; 20 mM KCl; 80 mM $MgSO_4$) is added into the assay plate. After being cleaved after for half an hour at room temperature, it is centrifuged at 3800 rpm for 15 minutes. 50 ul of lysate is taken into a new 96-well plate. Another 50 ul lysate is taken into 96-well PCR plates, and is put into a 96-well PCR instrument. It subjects to a heating treatment for 15 minutes at 50° C. It is transferred to another piece of 96-well plate. In the above-mentioned two plates, 100 ul of chromogenic solution (Tris, 100 mM, pH 8.0; TOOS solution, 15 mM; 4-APP, 0.5 mM; POD, 40 U/ml; fructose lysine, 15 mM) is added respectively. By the chromogenic treatment for 30 minutes, the absorbance value is recorded using a microplate reader. By calculating a ratio of both absorbances, the activity proportion of residual enzyme of crude enzyme solution after the heat treatment is determined. For mutant strains having improved thermostability, their theoretical activity residual rate will be higher than that of the wild type.

In the present invention, by screening more than 10000 mutant strains, six mutant strains with enhanced thermostability are obtained in total by screening. After the sequencing analysis, it is found that these six mutant strains are all single-base mutagenesis. Their nucleotide sequence mutageneses are 177G→T, 293A→C, 764G→C, 830A→C, 853G→C, 1063G→C, respectively. Corresponding amino acid sequence mutagenises are 59E→N, 98E→A, 225G→A, 277K→S, 285E→Q, and 355D→H, respectively.

Since mutagenesis of the above six sites have enhanced thermostability, if the above sites are mutated to other amino acids, the likelihood that the thermostability is higher than that of the wild type is also very high. Thus, the present invention tried numerous other mutagenesis of the above sites. At the same time, considering that if single site-directed mutageneses are superimposed, the thermostability may be further improved, a variety of combinations of different mutagenesis sites also have been tried.

For 59-site Glu, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that the thermostability of a vast majority of mutants has been improved, wherein improvements of thermostabilities of following mutants are significant, namely, L, I, V, F, M, W, T, C, N, Y, D, and H.

For 98-site Glu, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that the thermostability of a vast majority of mutants has been improved, wherein improvements of thermostabilities of following mutants are significant, namely, A, L I, V, P, F, S, T, C, N, Y, D, and H.

For the 225-site Gly, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that thermostability of a vast majority of mutants has been improved, wherein improvements of thermostabilities of following mutants are significant, namely, A, L, F, M, W, S. N, and D.

For the 277-site Lys, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that thermostability of a vast majority of mutants has been improved, wherein improvements of thermostabilities of following mutants are significant, namely. A, L, I, F, S, T, N, Y, R, and H.

For 277-site Lys, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that the thermostability of a vast majority of mutants has been improved, wherein improvements of thermostabilities of following mutants are significant, namely, A, L, I, F, S, T, N, Y, R, and H.

For 285-site Glu, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that the thermostability of a vast majority of mutants has been improved, wherein improvements of thermostabilities of following mutants are significant, namely, A, L, I, F, M, W, Q, and N.

For the 355-site Asp, by the site-directed mutagenesis method, it is substituted with other 19 kinds of amino acids respectively, so as to construct 19 kinds of mutant plasmids. These 19 kinds of mutant plasmids are transformed and expressed as strain BL21 (DE3) respectively. Cultivating, inducing, expressing, purifying, and enzymatic characteristic analysis are conducted. As a result, it is found that the thermostability of a vast majority of mutants has been improved, wherein improvements of thermostabilities of following mutants are significant, namely, L, I, V, F, M, W, T, C, Y, R, and H.

By specific analysis for the above sites, it is found that these sites indeed have a greater contribution to the thermostability of these enzymes. For this reason, it is considered that if different mutagenesis sites are combined, it is very likely that the thermostability of enzymes can be further improve. Thus, combinations of different mutagenesis sites are further conducted, such as a combination of 2 sites, a combination of 3 sites, a combination of 4 sites, a combination of 5 sites, a combination of 6 sites. However, since each site has ten or even more amino acid mutageneses that can be selected, combinations of different sites will be an astronomical figure. It is impossible to carry out research on each one. Therefore, merely mutagenesis combinations that are relatively representative can be selected, so as to illustrate that the combination of the above sites are effective.

For the combination of 2 mutagenesis sites, by the site-directed mutagenesis method, it is mutated into the following mutants: 59E→F, 98E→C; 59E→F, 225G→D; 59E→F, 277K→N; 59E→F, 285E→F; 98E→P, 225G→N; 98E→P, 277K→S; 225G→L, 277K→A; 225G→L, 285E→I; 277K→Y, 355D→T; 285E→I, 355D→W. The constructed mutant strains are transformed to BL2 (DE3). Cultivating, inducing, expressing, purifying, and enzymatic characteristic analysis are conducted. As a result, it is found that thermostabilities of these mutant strains have been further improved.

For the combination of 3 mutagenesis sites, by the site-directed mutagenesis method, it is mutated into the following mutants: 59E→F, 98E→C, 225G→F; 59E→F, 225G→D, 277K→N; 59E→F, 277K→N, 285E→I; 98E→P, 225G→N, 285E→Q; 225G→L, 285E→I, 355D→T. The constructed mutant strains are transformed to BL21 (DE3). Cultivating, inducing, expressing, purifying, and enzymatic characteristic analysis are conducted. As a result, it is found that thermostabilities of these mutant strains have been further improved.

For the combination of 4 mutagenesis sites, by the site-directed mutagenesis method, it is mutated into following mutants: 59E→F, 98E→C, 225G→F, 277K→N; 59E→F, 225G→D, 277K→N, 285E→F. The constructed mutant strains are transformed to BL21 (DE3). Cultivating, inducing, expressing, purifying, and enzymatic characteristic analysis are conducted. As a result, it is found that thermostabilities of these mutant strains have been further improved.

For the combination of 5 mutagenesis sites, by the site-directed mutagenesis method, it is mutated into following mutants: 59E→F, 98E→C, 225G→F, 277K→N, 285E→F. The constructed mutant strains are transformed to BL21 (DE3). Cultivating, inducing, expressing, purifying, and enzymatic characteristic analysis are conducted. As a result, it is found that thermostabilities of these mutant strains have been further improved.

For the combination of 6 mutagenesis sites, by the site-directed mutagenesis method, it is mutated into following mutants: 59E→F, 98E→C, 225G→F, 277K→N, 285E→F, 355D→L. The constructed mutant strains are transformed to BL21 (DE3). Cultivating, inducing, expressing, purifying, and enzymatic characteristic analysis are conducted. As a result, it is found that thermostabilities of these mutant strains have been further improved.

Meanwhile, as a common measure, between two sequences with a high homology, their structures and functions are usually similar. Beneficial effects obtained by mutating one of the sequences, the same mutagenesis conducted on the other sequence with a high homology usually can achieve similar beneficial effects. Generally speaking, the homology is more than 80%, preferably, more than 90%, more preferably, more than 96%, most preferably, more than 99%. Therefore, in the present invention, on the above basis, with respect to sequences that have a homology of equal or more than 80% with the amino acid sequence of Sequence 2, a great amount of researches on mutageneses and combinations thereof have been conducted.

Fructosyl amino acid oxidase from following several strains are selected as experimental subjects, so as to illustrate that enzymes homologies of more than 80% with Sequence 1, mutageneses on corresponding sites also lead to thermostabilities of these enzymes increased. These strains are: *Aspergillus niger* CBS513.88, *Aspergillus clavatus* NRRL1, *Neosartorya fischeri* NRRL181, and *Aspergillus fumigatus* Af293, respectively. Correspondingly, homologies with Sequence 1 are 80%, 83%, 96%, and 99%, respectively.

*Aspergillus clavatus* NRRL1 has a homology of 83% with Sequence 1, and its corresponding mutagenesis sites are 59E, 98E, 225G, 277N, 285E, and 355D. By selectively choosing several kinds of single amino acid mutagenesis, and several kinds of combinations of different sites mutageneses, it is found that thermostabilities of these enzymes do have different degrees of increase. For example, improvements of thermostabilities of following mutant strains are particularly evident: 59E→F, 98E→C, 225G→F, 285E→F, and 355D→L.

*Neosartorya fischeri* NRRL181 has a homology of 96% with Sequence 1, and its corresponding mutagenesis sites are 59E, 98E, 225G, 277K, 285E, and 355D. By selectively choosing several kinds of single amino acid mutagenesis, and several kinds of combinations of different sites mutageneses, it is found that thermostabilities of these enzymes do have different degrees of increase. For example, improvements of thermostabilities of following mutant strains are particularly evident: 59E→F, 98E→C, 225G→F, 277K→N, 285E→F, and 355D→L.

*Aspergillus fumigatus* Af293 has a homology of 99% with Sequence 1, and its corresponding mutagenesis sites are 59E, 98E, 225G, 277K, 285E, and 355D. By selectively choosing several kinds of single amino acid mutagenesis, and several kinds of combinations of different sites mutageneses, it is found that thermostabilities of these enzymes do have different degrees of increase. For example, improvements of thermostabilities of following mutant strains are particularly evident: 59E→F, 98E→C, 225G→F, 277K→N, 285E→F, and 355D→L.

In the present invention, mutageneses of amino acids are all substituted with Acronym character, which is common knowledge. Specific meanings are as follows: glycine G, alanine A, leucine L, isoleucine I, valine V, proline P, phenylalanine F, methionine M, tryptophan W, serine S, glutamine Q, threonine T, cysteine C, asparagine N, tyrosine Y, aspartic acid D, glutamic acid E, lysine K, arginine R, and histidine H. In the present invention, 285E→F, represents that 285-site glutamic acid is mutated into phenylalanine, and the rest are also similar.

Hereinafter, it should be noted that, the vector used by the present research is pET-22b, and the host bacteria (host cells) are BL21 (DE3). According to common sense, any simple alternations of vector, for example, pET-20b, pET-28b, pET-32a, pQE30, pTrc99a, and etc., or alternations of host bacteria, for example, Rosetta, Origami, M15, and etc., should be all construed as having the same technical effects, and should be all construed as falling into the scope of claims. Behaviors of adding purified tags or signal peptides on N or C-terminus of any mutant enzymes, should be also construed as falling into the scope of claims.

Generally, the well-known enzyme expression purification technology can be used for preparing fructosyl amino acid oxidases. For example, corresponding mutant strains are inoculated. After $OD_{600}$ grows to 0.5~1, isopropyl thiogalactoside (IPTG) induction is performed. In this case, in order to facilitate the expression, the low-temperature induction can be selected, such as 25° C., 20° C., 16° C., and etc. According to the induction temperature and the expression situation, an optimal induction time is determined, so as to obtain the optimal expression amount. After the expression, conventional methods can be used for centrifugation, sonic disruption, SDS-PAGE detection of the expression amount, and etc. As for purification, the tag carried by the recombinase can be used to select the appropriate method. For example, if a recombinant plasmid contains a His-tag, the nickel column can be used to for affinity purification.

The above fructosyl amino acid oxidases having good thermostabilities can be used to develop a detection method of glycated albumin, and to further develop glycated albumin test kit.

The main principle lies in that, an appropriate buffer being selected, under the action of a protease, the glycated albumin is degraded to fructosyl amino acids or fructosyl polypeptides. At this time, under the action of the fructosyl amino acid oxidases, fructosyl amino acids or fructosyl polypeptides are oxidized into fructose, glucose, or they are oxidized into peptides, hydrogen peroxide. A certain amount of oxygen is consumed at the same time. Then, by determining the generation of the product or the consumption amount of the substrate, the content of glycated albumin in the sample is calculated.

Sample requirements: in theory, as long as samples contain glycated albumin, glycated peptides, or glycated amino acids, they can be used as samples for testing. Since this method is mainly used in clinical tests, the common sample is the serum. Theoretically, hemolysis should be avoided. After samples are collected, they should be stored at 2~8° C. and promptly tested.

Buffer: buffers of any suitable concentration and pH can be used here, as long as they have no inhibition effect on the activity of the reaction during the test, and do not interfere with the test process. Typical buffers are: Tris hydrochloride buffer solution, acetic acid-sodium acetate buffer, phthalic acid-hydrochloric acid buffer, or glycine-hydrochloric acid buffer solution, and etc. The concentration of the buffer can be determined depending on circumstances, preferably, 20~200 mmol/L, more preferably, 50~100 mmol/L.

Protease: any protease capable of degrading glycated albumin can be used here, preferably trypsin, basophils, protease A, proteinase K, etc. The added protease should facilitate full degradation of glycated albumin. According to different sources, corresponding concentration should be 10~100 KU/L, preferably 40 KU/L.

Generation of product: there are three types of products generated: glucose, amino acids, and hydrogen peroxide. By determining the levels of any one of these three types of products, the content of glycated albumin can be calculated.

The determination of glucose can be performed by the hexokinase method. The principle is, under the effect of catalytic hexokinase, phosphorylation reaction occurs between glucose and ATP, producing glucose-6-phosphate (G-6-P) and ADP. Under the catalytic effect of Glucose-6-phosphate dehydrogenase (G6PD), the former is dehydrogenized, producing 6-phosphogluconate (6-GP). Meanwhile, NADP is reduced into NADPH. The rate of formation of NADPH is proportional to the concentration of glucose. The absorbance increase rate is monitored at a wavelength of 340 nm, so as to calculate the concentration of glucose.

By the reaction with fluorescamine, the fluorescence is eventually determined, so as to determine the amount of the amino acid.

The hydrogen peroxide can be detected by generating $H_2O_2$ through a coupling peroxidase, then generating the color through Trinder reaction. Here chromogen may be N, N-di(4-sulfobutyl)-3-methylaniline disodium salt (TODB), N-ethyl-N-(3-sulfopropyl)-3-methylaniline sodium salt (TOPS), and N-ethyl-N-(2-hydroxy-3-sulfopropyl)-3-methylaniline sodium salt (TOOS).

The consumption of substrate, the substrate mainly refers to $O_2$. The consumption of $O_2$ can be detected by the oxygen electrode.

With the above method, a corresponding glycated albumin test kit can be developed. The main principle lies in that, an appropriate buffer being selected, under the action of a protease, the glycated albumin is degraded to fructosyl amino acids or fructosyl polypeptides. At this time, under the action of the fructosyl amino acid oxidases, fructosyl amino acids or fructosyl polypeptides are oxidized into fructose, glucose, or they are oxidized into peptides or hydrogen peroxide. A Certain amount of oxygen is consumed at the same time. Then, by determining the generation of the product or the consumption of the substrate, the content of glycated albumin in the sample is calculated. In practice, the most common method is detecting the hydrogen peroxide in the product, that is, detecting through Trinder reaction. This is the coupling manner currently used in the vast majority of test kits. Embodiments in the present specification focus on using this method to perform the experiment, so as to illustrate. However, detecting other substances to achieve the detection of glycated albumin in the test kit is not excluded.

This glycated albumin test kit includes reagent 1 and reagent 2. Reagent 1 contains a buffer, protease, peroxidase, 4-amino antipyrine, and preservatives. Reagent 2 contains a buffer, fructosyl amino acid oxidases mutant strains, the chromogen, preservatives.

Buffer: buffers of any suitable concentration and pH can be used here, as long as they have no inhibition effect on the activity of the reaction during the test, and do not interfere with the test process. Typical buffers are: Tris hydrochloride buffer solution, acetic acid-sodium acetate buffer, phthalic acid-hydrochloric acid buffer, or glycine-hydrochloric acid buffer solution, and etc. The concentration of the buffer can be determined depending on circumstances, preferably, 20~200 mmol/L, more preferably, 50~100 mmol/L.

Protease: any protease capable of degrading glycated albumin can be used here, preferably, trypsin, basophils, protease A, proteinase K, and etc. The added protease should facilitate full degradation of glycated albumin. According to different sources, corresponding concentration should be 10~100 KU/L, preferably 40 KU/L.

Peroxidase: this enzyme functions as coupling. The concentration of 10~100 KU/L can be added according to requirements, preferably, 30 KU/L.

The purpose of preservatives is to avoid the breeding of bacteria in the test kit, so as to ensure that the sensitivity and etc. of the test kit will not be affected for long-term preservation. Preservatives include 2-methyl-4-isothiazolin-3-one, proclin 300, and etc. To effectively achieve this object, the adding amount of preservatives should be 0.01~0.05%, preferably 0.02%.

Said fructosyl amino acid oxidases refer to fructosyl amino acid oxidases with high thermostabilities of the present invention. The adding amount of these enzymes should be able to make the substrate fructosyl amino acids or fructosyl polypeptides sufficiently react. The adding amount should be 10~100 KU/L, preferably, 20~50 KU/L, most preferably, 28 KU/L.

The chromogen of the present invention may be N, N-di(4-sulfobutyl)-3-methylaniline disodium salt (TODB), N-ethyl-N-(3-sulfopropyl) sodium 3-methylaniline (TOPS), and N-ethyl-N-(2-hydroxy-3-sulfopropyl)-3-methylaniline sodium salt (TOOS,). The concentration of the chromogen in the test kit may be 1~10 mmol/L, preferably 2 mmol/L.

The above test kit for determining glycated albumin of the present invention, the test kit includes reagent 1 and reagent 2, wherein concentrations of components of the reagents are:
reagent 1:
buffer 20~200 mmol/L,
protease 10~100 KU/L,
peroxidase 10~100 KU/L,
4-amino-antipyrine 5~50 mM/L, and
preservative 0.01 to 0.05%;
reagent 2:
buffer 20~200 mmol/L,
fructosyl amino acid oxidases obtained after amino acid of one or more of the above six sites is substituted 10~100 KU/L
chromogen 1~10 mmol/L, and
preservative 0.01 to 0.05%.

If the detection of glycated albumin of the present invention and the detection of albumin are combined, a percentage value of the glycated albumin can be obtained through calculating the glycated albumin concentration divided by the albumin concentration.

Since its performance is better than prior fructosyl amino acid oxidases, not only that the test kit meets the requirement in terms of sensitivity, interference, and etc., but also that all aspects of performance do not significantly decrease after long-term preservation.

The present invention provides a stable, simple, fast, sensitive and accurate quantitative detection reagents, whose detection has good dilution linearity, accuracy, precision, and has a good consistency with HPLC test. Compared with the prior art, in the glycated albumin test kit using the present invention, glycated albumin is determined by the enzyme method. It can completely replace the HPLC, to be applied to clinical laboratories, to perform tremendous sample testing. Its operation is simple, with a wide linear range, low cost. It is very valuable in practice.

DETAILED DESCRIPTION

Figure 1:
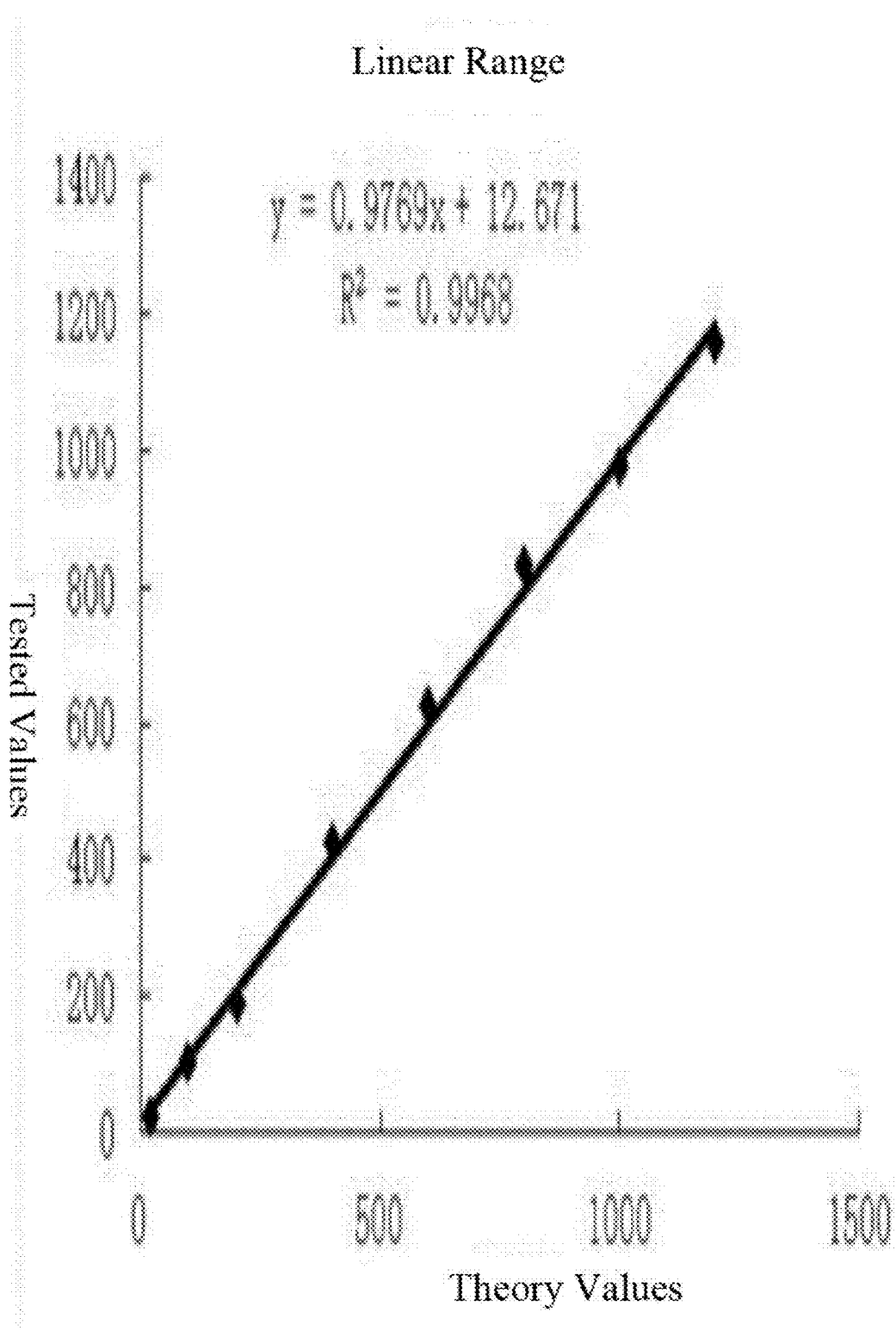
FIG. 1 is a glycated albumin detecting linear range diagram.
Figure 2:
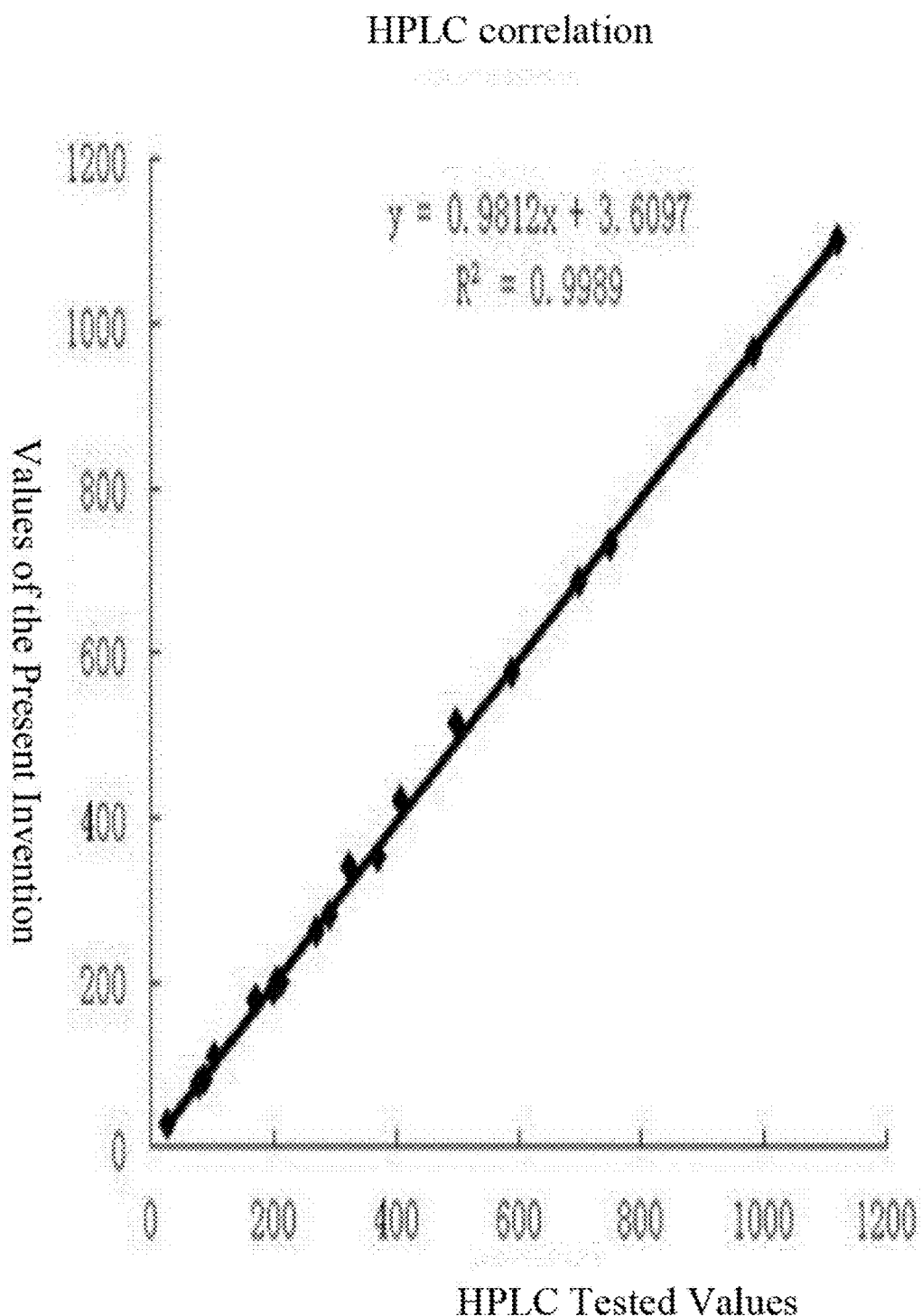
FIG. 2 is a diagram of correlation of the present invention with HPLC detection.

The present invention is further illustrated below with reference to Embodiments. However, the present invention is not limited to the following Embodiments.

Embodiment One

Construction of mutagenesis libraries

1. For the sequence shown in Sequence 2, using whole gene synthesis method to perform the synthesis, and it is cloned into pET-22b vector. Restriction sites NdeI and XhoI are used. Thereby obtained plasmid pET-Ama is the following error-prone PCR and WHOP-PCR template.

2. Error-Prone PCR Reaction System and Conditions

TABLE 1

| Reaction system is 100 ul: | |
| --- | --- |
| Name | Volume (ul) |
| dNTP Mixture (2.5 mM for each) | 8 |
| dTTP (100 mM) | 0.8 |
| dCTP (100 mM) | 0.8 |
| 10 * PCR Buffer | 10 |
| Upstream primer (5 mM), sequence 3 | 20 |
| Downstream primer (5 mM), sequence 4 | 20 |
| $MnCl_2$ (5 mM) | 10 |
| $Mg^{2+}$ (25 mM) | 14 |
| Taq Enzyme (5 U/ul) | 1 |
| Template (10 ng/ul) | 5 |
| Water | 12 |

Reaction conditions are:
95° C. 5 min; 94° C. 30 sec; 55° C. 30 sec; 72° C. 2 min; 30 cycles; 72° C. 10 min; 4° C. preservation.

The amount of the above MnCl$_2$ can be adjusted as appropriate, in order to obtain a suitable mutagenesis frequency, i.e., 1 to 2 nucleotide mutageneses/1 Kb nucleotides.

3. WHOP-PCR reaction system and conditions

The error-prone PCR fragment with the size of about 1.4 Kb is recycled using gel, and is used as primers in the next round WHOP-PCR.

TABLE 2

WHOP-PCR reaction system, 50 ul:

| Name | Volume (ul) |
|---|---|
| dNTP Mixture (2.5 mM for each) | 4 |
| 5 * HF Buffer | 10 |
| error-prone PCR fragments (25 ng/ul) | 20 |
| Phusion Hot Start II High-Fidelity DNA Polymerase (5 U/ul) | 0.5 |
| Template (20 ng/ul) | 5 |
| Water | 10.5 |

WHOP-PCR reaction conditions:

98° C. 30 sec; 98° C. 10 sec; 60° C. 10 sec; 72° C. 2.5 min; 24 cycles; 72° C. 5 min; 4° C. preservation.

4. Digestion and transformation 1 ul of DpnI is added into 50 ul of WHOP-PCR product, to perform the enzyme digestion. At 37° C., the reaction lasts for 2 hours to completely remove the template DNA.

The digested product described above is divided into five tubes and transformed into TOP10 competent cells. The next day, a total library capacity of more than 10000 monoclone is obtained.

Embodiment Two

Mutagenesis libraries screening

1. Cultivating, inducing, and expressing

The obtained clones, after mixing by a coating stick, are collected in a centrifuge tube. Plasmids are extracted. The obtained plasmids are transformed into BL21 (ED3), to be ready for the next screening use. Next, the transformants are inoculated in a 96-well plate, wherein the last well is inoculated with a wild-type strain as a control. The cultivation medium is 150 ul LB/per well, containing the antibiotic ampicillin. This well plate is used as a retention plate. The next day, in the same order, it is transferred to another 96-well plate. The cultivation medium is 150 ul LB/per well. Meanwhile, the antibiotic ampicillin and IPTG are added for induction. It is cultivated at 37 (C for 6 hours. Bacteria is harvested by a centrifugation of 3800 rpm. The medium is removed. This plate is used as an assay plate.

2. Screening 150 ul lysis solution (100 mM Tris, pH 8.0; 0.4 mg/ml sodium deoxycholate; 0.8 mg/ml CTAB; 20 m MKCl; 80 mM MgSO4) is added to the assay plate. After lysis at room temperature for half an hour, it is centrifuged at 3800 rpm for 15 minutes. Another 50 ul lysate is added to a new 96-well plate. Another 50 ul of lysis solution is taken in a 96-well PCR plate, which is placed in a 96-well PCR instrument. It is heat-treated at 50° C. for 15 minutes. It is transferred to another 96-well plate. In the above-mentioned two plates, 100 ul of chromogenic solution (Tris, 100 mM, pH8.0; TOOS solution, 15 mM; 4-APP, 0.5 mM; POD, 40 U/ml; fructose lysine, 15 mM) is added respectively. By the chromogenic treatment for 30 minutes, the absorbance value is recorded using a microplate reader. By calculating a ratio of both absorbance, the activity proportion of residual enzyme of crude enzyme solution after the heat treatment is determined. For mutant strains having improved thermostability, their theoretical activity residual rate will be higher than that of the wild type.

In the present invention, by screening more than 10000 mutant strains, six mutant strains with enhanced thermostability are obtained in total by screening. After the sequencing analysis, it is found that these six mutant strains are all single-base mutageneses. Their nucleotide sequence mutageneses are 177G→T, 293A→C, 764G→C, 830A→C, 853G→C, 1063G→C, respectively. Corresponding amino acid sequence mutagenises are 59E→N, 98E→A, 225G→A, 277K→S, 285E→Q, and 355D→H, respectively.

Embodiment Three

Determination of fructosyl amino acid oxidases activity and thermostability analysis In a buffer of 100 mM Tris, pH 8.0, purified fructosyl amino acid oxidase is diluted to approximately 10 ug/ml.

50 ul of fructosyl amino acid oxidase is taken into a 96-well PCR. It is heat-treated at 50° C. for 15 min. It is stored under 4° C.

50 ul of heat-treated fructosyl amino acid oxidase is transferred to a 96-well plate. Meanwhile, unheated 50 ul fructosyl amino acid oxidase is taken to a 96-well plate. It is incubated at 37° C. for 10 min.

Color developing solution which has previously been incubated to 37° C. (Tris, 100 mM, pH 8.0; TOOS solution, 15 mM; 4-APP, 0.5 mM; POD, 40 U/ml; fructose lysine, 15 mM) is added. The reaction is conducted at 37° C. for 30 min.

The absorbance at 555 nm is recorded using a microplate reader.

The absorbance value of heat-treated fructosyl amino acid oxidase is divided by the absorbance value of non-heat-treated fructosyl amino acid oxidase. The resulting value is the ratio of residual activity at this temperature.

Thermostability analysis is performed on these six mutant strains obtained from random mutageneses and wild-type fructosyl amino acid oxidases. The results are shown in Table 3.

TABLE 3

Thermostability analysis of mutant strains obtained from random mutageneses

| Plasmid | Amino mutagenesis | 50° C., 15 min, Activity ratio of residual enzyme |
|---|---|---|
| pET-Ama | None | 5% |
| pET-Ama-59N | E→N | 15% |
| pET-Ama-98A | E→A | 39% |
| pET-Ama-225A | G→A | 31% |
| pET-Ama-277S | K→S | 34% |
| pET-Ama-285Q | E→Q | 38% |
| pET-Ama-355H | D→H | 28% |

Embodiment Four

Thermostability analysis of 59-site amino acid substitution

1. Introducing 59-site amino acid site-directed mutagenesis

In the first round of the PCR, pET-Ama is used as a template, primer sequence 5 (5'-tgctagttattgctcagcgg-3'), Sequence 6 (5'-acaagattatgttacacagcgagctg-3') containing the site-directed mutagenesis are used as upstream primers respectively. Fragment containing site-directed mutagenesis is obtained. PCR system is 50 ul:

TABLE 4

PCR system

| Name | Volume (ul) |
|---|---|
| dNTP Mixture (2.5 mM for each) | 4 |
| 5 * HF Buffer | 10 |
| Upstream primer, sequence 6 (5 pm/ul) | 10 |
| T7-Ter, sequence 5 (5 pm/ul) | 10 |
| Phusion Hot Start II High-Fidelity DNA Polymerase (5 U/ul) | 0.5 |
| Template (1 ng/ul) | 5 |
| Water | 10.5 |

PCR reaction conditions are:

98° C. 30 sec; 98° C. 10 sec; 60° C. 10 sec; 72° C. 30 sec; 30 cycles; 72° C. 5 min; 4° C. preservation.

After the obtained target fragment is purified, it is used as a primer in the next round WHOP-PCR. Specific reaction system is shown in Table 5

TABLE 5

WHOP-PCR reaction system

| Name | Volume (ul) |
|---|---|
| dNTP Mixture (2.5 mM for each) | 4 |
| 5 * HF Buffer | 10 |
| Target PCR production (25 ng/ul) | 20 |
| Phusion Hot Start II High-Fidelity DNA Polymerase (5 U/ul) | 0.5 |
| TemplatepET-Ama (20 ng/ul) | 5 |
| Water | 10.5 |

PCR reaction conditions are:

98° C. 30 sec; 98° C. 10 sec; 60° C. 10 sec; 72° C. 2.5 min; 24 cycles; 72° C. 5 min; 4° C. preservation.

1 ul of DpnI is added into 50 ul of WHOP-PCR product to perform enzyme digestion. The reaction last for 2 hours under 37° C., so that the template DNA is removed completely. Then, BL21 (DE3) is transformed. After sequencing correctly, it is used for thermostability analysis.

Thermostability after 2.59-site amino acid substitution

The obtained mutant is inoculated overnight. The next day, in a proportion of 1%, it is transferred to a fresh LB medium containing ampicillin. After $OD_{600}$ grows to about 0.8, IPTG with a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 6

Thermostability analysis of 59-site amino acid substitution

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M1 | pET-Ama-59L | E→L | pET-Ama | 5, 6 | 32% |
| M2 | pET-Ama-59I | E→I | pET-Ama | 5, 7 | 50% |
| M3 | pET-Ama-59V | E→V | pET-Ama | 5, 8 | 20% |
| M4 | pET-Ama-59F | E→F | pET-Ama | 5, 9 | 60% |
| M5 | pET-Ama-59M | E→M | pET-Ama | 5, 10 | 42% |
| M6 | pET-Ama-59W | E→W | pET-Ama | 5, 11 | 55% |
| M7 | pET-Ama-59T | E→T | pET-Ama | 5, 12 | 38% |
| M8 | pET-Ama-59C | E→C | pET-Ama | 5, 13 | 25% |
| M9 | pET-Ama-59N | E→N | pET-Ama | 5, 14 | 15% |
| M10 | pET-Ama-59Y | E→Y | pET-Ama | 5, 15 | 58% |
| M11 | pET-Ama-59D | E→D | pET-Ama | 5, 16 | 18% |
| M12 | pET-Ama-59H | E→H | pET-Ama | 5, 17 | 30% |

Embodiment Five

Thermostability analysis of 98-site amino acid substitution

According to the above method, different site-directed mutageneses are introduced in the 98-site amino acid. The obtained mutant is inoculated overnight. The next day, in a proportion of 1%, it is transferred to a fresh LB medium containing ampicillin. After $OD_{600}$ grown to about 0.8, IPTG with a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 7

Thermostability analysis of 98-site amino acid substitution

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M13 | pET-Ama-98A | E→A | pET-Ama | 5, 18 | 39% |
| M14 | pET-Ama-98L | E→L | pET-Ama | 5, 19 | 22% |
| M15 | pET-Ama-98I | E→I | pET-Ama | 5, 20 | 40% |
| M16 | pET-Ama-98V | E→V | pET-Ama | 5, 21 | 55% |
| M17 | pET-Ama-98P | E→P | pET-Ama | 5, 22 | 61% |
| M18 | pET-Ama-98F | E→F | pET-Ama | 5, 23 | 33% |
| M19 | pET-Ama-98S | E→S | pET-Ama | 5, 24 | 60% |
| M20 | pET-Ama-98T | E→T | pET-Ama | 5, 25 | 20% |
| M21 | pET-Ama-98C | E→C | pET-Ama | 5, 26 | 44% |
| M22 | pET-Ama-98N | E→N | pET-Ama | 5, 27 | 42% |
| M23 | pET-Ama-98Y | E→Y | pET-Ama | 5, 28 | 25% |
| M24 | pET-Ama-98D | E→D | pET-Ama | 5, 29 | 45% |
| M25 | pET-Ama-98H | E→H | pET-Ama | 5, 30 | 18% |

Embodiment Six

Thermostability analysis of 225-site amino acid substitution

According to the above method, different site-directed mutageneses are introduced in 225-site amino acid. The obtained mutant is inoculated overnight. The next day, in a proportion of 1%, it is transferred to a fresh LB medium containing ampicillin. After $OD_{600}$ grows to about 0.8, IPTG with a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 8

Thermostability analysis of 225-site amino acid substitution

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M26 | pET-Ama-225A | G→A | pET-Ama | 5, 31 | 31% |
| M27 | pET-Ama-225L | G→L | pET-Ama | 5, 32 | 28% |
| M28 | pET-Ama-225F | G→F | pET-Ama | 5, 33 | 44% |
| M29 | pET-Ama-225M | G→M | pET-Ama | 5, 34 | 14% |
| M30 | pET-Ama-225W | G→W | pET-Ama | 5, 35 | 18% |
| M31 | pET-Ama-225S | G→S | pET-Ama | 5, 36 | 22% |
| M32 | pET-Ama-225N | G→N | pET-Ama | 5, 37 | 16% |
| M33 | pET-Ama-225D | G→D | pET-Ama | 5, 38 | 28% |

Embodiment Seven

Thermostability analysis of 277-site amino acid substitution

According to the above method, different site-directed mutageneses are introduced in 277-site amino acid. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 9

Thermostability analysis of 277-site amino acid substitution

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M34 | pET-Ama-277A | K→A | pET-Ama | 5, 39 | 36% |
| M35 | pET-Ama-277L | K→L | pET-Ama | 5, 40 | 59% |
| M36 | pET-Ama-277I | K→I | pET-Ama | 5, 41 | 28% |
| M37 | pET-Ama-277F | K→F | pET-Ama | 5, 42 | 47% |
| M38 | pET-Ama-277S | K→S | pET-Ama | 5, 43 | 34% |
| M39 | pET-Ama-277T | K→T | pET-Ama | 5, 44 | 44% |
| M40 | pET-Ama-277N | K→N | pET-Ama | 5, 45 | 48% |
| M41 | pET-Ama-277Y | K→Y | pET-Ama | 5, 46 | 49% |
| M42 | pET-Ama-277R | K→R | pET-Ama | 5, 47 | 23% |
| M43 | pET-Ama-277H | K→H | pET-Ama | 5, 48 | 59% |

Embodiment Eight

Thermostability analysis of 285-site amino acid substitution

According to the above method, different site-directed mutageneses are introduced in 285-site amino acid. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 10

Thermostability analysis of 285-site amino acid substitution

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M44 | pET-Ama-285A | E→A | pET-Ama | 5, 49 | 20% |
| M45 | pET-Ama-285L | E→L | pET-Ama | 5, 50 | 46% |
| M46 | pET-Ama-285I | E→I | pET-Ama | 5, 51 | 43% |
| M47 | pET-Ama-285F | E→F | pET-Ama | 5, 52 | 52% |
| M48 | pET-Ama-285M | E→M | pET-Ama | 5, 53 | 21% |
| M49 | pET-Ama-285W | E→W | pET-Ama | 5, 54 | 13% |
| M50 | pET-Ama-285Q | E→Q | pET-Ama | 5, 55 | 38% |
| M51 | pET-Ama-285N | E→N | pET-Ama | 5, 56 | 29% |

Embodiment Nine

Thermostability analysis of 355-site amino acid substitution

According to the above method, different site-directed mutageneses are introduced in the 355-site amino acids. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 11

Thermostability analysis of 355-site amino acid substitution

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M52 | pET-Ama-355L | D→L | pET-Ama | 5, 57 | 55% |
| M53 | pET-Ama-355I | D→I | pET-Ama | 5, 58 | 31% |
| M54 | pET-Ama-355V | D→V | pET-Ama | 5, 59 | 36% |
| M55 | pET-Ama-355F | D→F | pET-Ama | 5, 60 | 34% |
| M56 | pET-Ama-355M | D→M | pET-Ama | 5, 61 | 43% |
| M57 | pET-Ama-355W | D→W | pET-Ama | 5, 62 | 26% |

TABLE 11-continued

Thermostability analysis of 355-site amino acid substitution

| Number of mutant enzyme | Plasmid | Amino acid mutageneses | Template | Primers sequence | 50° C., 15 min, Activity ratio of residual enzyme |
|---|---|---|---|---|---|
| M58 | pET-Ama-355T | D→T | pET-Ama | 5, 63 | 41% |
| M59 | pET-Ama-355C | D→C | pET-Ama | 5, 64 | 39% |
| M60 | pET-Ama-355Y | D→Y | pET-Ama | 5, 65 | 35% |
| M61 | pET-Ama-355R | D→R | pET-Ama | 5, 66 | 20% |
| M62 | pET-Ama-355H | D→H | pET-Ama | 5, 67 | 78% |

Embodiment Ten

Thermostability analysis of a combination of amino acid substitutions on two different mutagenesis sites According to the above method, different site-directed mutageneses are introduced on two different sites of the amino acid. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 12

Thermostability analysis of amino acid substitutions on two different mutagenesis sites

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M63 | pET-Ama-59F98C | 59E→F, 98E→C | pET-Ama-59F | 5, 26 | 74% |
| M64 | pET-Ama-59F225D | 59E→F, 225G→D | pET-Ama-59F | 5, 38 | 72% |
| M65 | pET-Ama-59F277N | 59E→F, 277K→N | pET-Ama-59F | 5, 45 | 76% |
| M66 | pET-Ama-59F285F | 59E→F, 285E→F, | pET-Ama-59F | 5, 52 | 77% |
| M67 | pET-Ama-98P225N | 98E→P, 225G→N | pET-Ama-98P | 5, 56 | 69% |
| M68 | pET-Ama-98P277S | 98E→P, 277K→S | pET-Ama-98P | 5, 43 | 70% |
| M69 | pET-Ama-225L277A | 225G→L, 277K→A | pET-Ama-225L | 5, 39 | 51% |
| M70 | pET-Ama-225L285I | 225G→L, 285E→I | pET-Ama-225L | 5, 51 | 55% |
| M71 | pET-Ama-277Y355T | 277K→Y, 355D→T | pET-Ama-277Y | 5, 63 | 59% |
| M72 | pET-Ama-285I355W | 285E→I, 355D→W | pET-Ama-285I | 5, 62 | 62% |

Embodiment Eleven

Thermostability analysis of a combination of amino acid substitutions on three different mutagenesis sites According to the above method, different site-directed mutageneses are introduced on three different sites of the amino acid. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 13

Thermostability analysis of a combination of amino acid substitutions on three different mutagenesis sites

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M73 | pET-Ama-59F98C225F | 59E→F, 98E→C, 225G→F | pET-Ama-59F98C | 5, 33 | 85% |
| M74 | pET-Ama-59F225D277N | 59E→F, 225G→D, 277 K→N | pET-Ama-59F225D | 5, 45 | 83% |
| M75 | pET-Ama-59F277N285I | 59E→F, 277K→N, 285E→I | pET-Ama-59F277N | 5, 51 | 83% |
| M76 | pET-Ama-98P225N285Q | 98E→P, 225G→N, 285E→Q | pET-Ama-98P225N | 5, 55 | 79% |
| M77 | pET-Ama-225L285I355T | 225G→L, 285E→I, 355D→T | pET-Ama-225L285I | 5, 63 | 75% |

Embodiment Twelve

Thermostability analysis of a combination of amino acid substitutions on four different mutagenesis sites According to the above method, different site-directed mutageneses are introduced on four different sites of the amino acid. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 14

Thermostability analysis of amino acid substitutions on four different mutagenesis sites

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M78 | pET-Ama-59F98C225F277N | 59E→F, 98E→C, 225G→F, 277K→N | pET-Ama-59F98C225F | 5, 45 | 92% |
| M79 | pET-Ama-59F225D277N285F | 59E→F, 225G→D, 277 K→N, 285E→F | pET-Ama-59F225D277N | 5, 52 | 93% |

Embodiment Thirteen

Thermostability analysis of a combination of amino acid substitutions on five different mutagenesis sites According to the above method, different site-directed mutageneses are introduced on five different sites of amino acids. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 15

Thermostability analysis of amino acid substitutions on five different mutagenesis sites

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M80 | pET-Ama-59F98C225F277N285F | 59E→F, 98E→C, 225G→F, 277K→N, 285E→F | pET-Ama-59F98C225F277N | 5, 52 | >96% |

Embodiment Fourteen

Thermostability analysis of a combination of amino acid substitutions on six different mutagenesis sites According to the above method, different site-directed mutageneses are introduced on six different sites of amino acid. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 16

Thermostability analysis of amino acid substitutions on six different mutagenesis sites

| Number of mutant enzyme | Plasmid | Amino acid mutageneses | Template | Primers sequence | 50° C., 15 min, Activity ratio of residual enzyme |
|---|---|---|---|---|---|
| WT1 | pET-Ama | / | / | / | 5% |
| M81 | pET-Ama-59F98C225F277N285F355L | 59E→F, 98E→C, 225G→F, | pET-Ama-59F98C225F277N283F | 5, 57 | >98% |

TABLE 16-continued

Thermostability analysis of amino acid substitutions on six different mutagenesis sites

| Number of mutant enzyme | Plasmid | Amino acid mutageneses | Template | Primers sequence | 50° C., 15 min, Activity ratio of residual enzyme |
|---|---|---|---|---|---|
| | | 277K→N, 285E→F, 355D→L | | | |

Embodiment Fifteen

Thermostability analysis of mutageneses of fructosyl amino acid oxidases from *Aspergillus niger* CBS513.88 and the combination thereof As is known from Blast, the amino acid sequence of fructosyl amino acid oxidases from *Aspergillus niger* CBS513.88 and the amino acid sequence of fructosyl amino acid oxidases from *Aspergillus fumigatus* have a homology of 80%. Its amino acid sequence is shown a sequence 68. The nucleotide sequence of the sequence 69 is shown. Use whole gene synthesis method, sequences 69 are synthesized, and cloned into the NdeI and XhoI restriction sites of pET-22b vector.

After the sequence analysis, it is found that, corresponding to amino acids of sites 59, 98, 225, 277, 285, and 355 of Amadoriase I, corresponding sites on fructosyl amino acid oxidases of *Aspergillus niger* CBS513.88 are 59E, 98E, 225G, 277K, 285E, and 355D.

According to the above method of site-directed mutagenesis, these sites of fructosyl amino acid oxidases of *Aspergillus niger* CBS513.88 is single-base mutated or mutated on a combination of different sites. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 17

Thermostability analysis of amino acid substitutions of fructosyl amino acid oxidases of *Aspergillus niger* CBS513.88

| Number of mutant enzyme | Amino acid mutageneses | 50° C., 15 min, Activity ratio of residual enzyme |
|---|---|---|
| WT2 | / | <5% |
| M82 | 59E→F | 20% |
| M83 | 98E→C | 22% |
| M84 | 225G→F | 30% |
| M85 | 277K→N | 38% |
| M86 | 285E→F | 32% |
| M87 | 355D→L | 26% |
| M88 | 59E→F, 98E→C, | 37% |
| M89 | 59E→F, 98E→C, 225G→F, | 51% |
| M90 | 59E→F, 98E→C, 225G→F, 277K→N, | 75% |
| M91 | 59E→F, 98E→C, 225G→F, 277K→N, 285E→F, | 93% |
| M92 | 59E→F, 98E→C, 225G→F, 277K→N, 285E→F, 355D→L | >98% |

Embodiment Sixteen

Thermostability analysis of mutageneses of fructosyl amino acid oxidases from *Aspergillus clavatus* NRRL1 and the combination thereof As is known from Blast, the amino acid sequence of fructosyl amino acid oxidases from *Aspergillus clavatus* NRRL1 and the amino acid sequence of fructosyl amino acid oxidases from *Aspergillus fumigatus* have a homology of 83%. Its amino acid sequence is shown in sequence 70. The nucleotide sequence is shown in sequence 71. Using whole gene synthesis method, sequences 71 is synthesized and cloned into the NdeI and XhoI restriction sites of pET-22b vector.

After the sequence analysis, it is found that, corresponding to amino acids of sites 59, 98, 225, 277, 285, and 355 of Amadoriase I, corresponding sites on fructosyl amino acid oxidases of *Aspergillus clavatus* NRRL1 are 59E, 98E, 225G, 277N, 285E, and 355D.

According to the above method of site-directed mutagenesis, these sites of fructosyl amino acid oxidases of *Aspergillus clavatus* NRRL1 are single-base mutagenesis or mutated on a combination of different sites. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 18

Thermostability of amino acid substitutions of fructose amino acid oxidase of *Aspergillus clavatus* NRRL1

| Number of mutant enzyme | Amino acid mutageneses | 50° C., 15 min, Activity ratio of residual enzyme |
|---|---|---|
| WT3 | / | <5% |
| M93 | 59E→F | 30% |
| M94 | 98E→C | 26% |
| M95 | 225G→F | 37% |
| M96 | 285E→F | 36% |
| M97 | 355D→L | 46% |
| M98 | 59E→F, 98E→C, | 47% |
| M99 | 59E→F, 98E→C, 225G→F, | 65% |
| M100 | 59E→F, 98E→C, 225G→F, 285E→F, | 90% |
| M101 | 59E→F, 98E→C, 225G→F, 285E→F, 355D→L | >95% |

Embodiment Seventeen

Thermostability analysis of mutageneses of fructosyl amino acid oxidases from *Neosartorya fischeri* NRRL181 and the combination thereof As is known from Blast, the amino acid sequence of fructosyl amino acid oxidases derived from *Neosartorya fischeri* NRRL181 and the amino acid sequence of fructosyl amino acid oxidases from *Aspergillus fumigatus* have a homology of 96%. Its amino acid sequence is shown in sequence 72. The nucleotide sequence is shown in sequence 73. Using whole gene synthesis method, sequences 73 is synthesized and cloned into the NdeI and XhoI restriction sites of vector pET-22b.

After the sequence analysis, it is found that, corresponding to amino acids of sites 59, 98, 225, 277, 285, and 355 of Amadoriase I, corresponding sites on fructosyl amino acid oxidases of *Neosartorya fischeri* NRRL181 are 59E, 98E, 225G, 277K, 285E, and 355D.

According to the above method of site-directed mutagenesis, these sites of fructosyl amino acid oxidases of *Neosartorya fischeri* NRRL181 are single-base mutated or mutated on a combination of different sites. The obtained mutant is inoculated overnight. The next day, in a proportion of 1%, it is transferred to LB medium containing ampicillin. After $OD_{600}$ grows to about 0.8, IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 19

Thermostability analysis of amino acid substitutions of fructosyl amino acid oxidases of *Neosartorya fischeri* NRRL181

| Number of mutant enzyme | Amino acid mutageneses | 50° C., 15 min, Activity ratio of residual enzyme |
|---|---|---|
| WT4 | / | <5% |
| M102 | 59E→F | 33% |
| M103 | 98E→C | 42% |
| M104 | 225G→F | 29% |
| M105 | 277K→N | 35% |
| M106 | 285E→F | 55% |
| M107 | 355D→L | 44% |
| M108 | 59E→F, 98E→C, | 61% |
| M109 | 59E→F, 98E→C, 225G→F, | 72% |
| M110 | 59E→F, 98E→C, 225G→F, 277K→N, | 88% |
| M111 | 59E→F, 98E→C, 225G→F, 277K→N, 285E→F, | 94% |
| M112 | 59E→F, 98E→C, 225G→F, 277K→N, 285E→F, 355D→L | >98% |

Embodiment Eighteen

Thermostability analysis of mutageneses of the fructose amino acid from *Aspergillus fumigatus* Af293 and the combination thereof As is known from Blast, the amino acid sequence of fructosyl amino acid oxidases from the amino acid sequence of *Aspergillus fumigatus* A1293 and fructosyl amino acid oxidases from *Aspergillus fumigatus* have a homology of 99%. Its amino acid sequence is shown in sequence 74. The nucleotide sequence is shown in sequence 75. Using whole gene synthesis method, sequences 75 is synthesized, and is cloned into the NdeI and XhoI restriction sites of pET-22b vector.

After the sequence analysis, it is found that, corresponding to amino acids of sites 59, 98, 225, 277, 285, and 355 of Amadoriase I, corresponding sites on fructosyl amino acid oxidases of the *Aspergillus fumigatus* CBS513.88 are 59E, 98E 225G, 277K, 285E, and 355D.

According to the above method of site-directed mutagenesis, these sites of fructosyl amino acid oxidases of *Aspergillus fumigatus* Af293 are single-base mutated or mutated on a combination of different sites. The obtained mutant is inoculated overnight. The next day, in a proportion of 1%, it is transferred to LB medium containing ampicillin. After $OD_{600}$ grows to about 0.8. IPTG having a final concentration of 0.4 mM is added. It is induced for about five hours. Bacteria are harvested by centrifugation, broken, and purified. Thermostability analysis as described above is performed on purified fructosyl amino acid oxidases. Detailed results are shown in the table below.

TABLE 20

Thermostability analysis of amino acid substitutions of fructosyl amino acid oxidases of *Aspergillus fumigatus* Af293

| Number of mutant enzyme | Amino acid mutageneses | 50° C., 15 min, Activity ratio of residual enzyme |
|---|---|---|
| WT5 | / | <5% |
| M113 | 59E→F | 50% |
| M114 | 98E→C | 42% |
| M115 | 225G→F | 40% |
| M116 | 277K→N | 41% |
| M117 | 285E→F | 55% |
| M118 | 355D→L | 48% |
| M119 | 59E→F, 98E→C, | 67% |
| M120 | 59E→F, 98E→C, 225G→F, | 82% |
| M121 | 59E→F, 98E→C, 225G→F, 277K→N, | 90% |
| M123 | 59E→F, 98E→C, 225G→F, 277K→N, 285E→F, 355D→L | >98% |

Embodiment Nineteen

Preparation Method

1. Obtaining the strain: when the strain containing different mutated genes has been cultivated to $OD_{600}$ of about 0.8, IPTG is added. It is induced for 5 hours. The strain is harvested by centrifugation. The collected strain is re-suspended with the buffer, and is ultrasonically disrupted. The supernatant is collected by centrifugation.

2. Ammonium sulfate precipitation: using an ammonium sulfate solution, the supernatant obtained in step (1) is subjected to fractional precipitation. The final collected and obtained precipitate is dissolved in buffer A, so as to obtain a crude extracted solution.

Affinity chromatography: using buffer A balanced nickel column, the crude extract solution obtained in step (2) is adsorbed on a nickel column. After the absorption finishes, gradient elution is performed with an imidazole solution. The eluent is collected.

4. Dialysis: the eluate in step (3) is put into a dialysis bag. It is put in a dialysate at 4° C., and is dialyzed overnight with magnetic stirring.

Buffer A in step (2) is: 50 mM potassium phosphate buffer, pH 8.0, 500 mM NaCl.

Imidazole solution in step (3) is: 50 mM potassium phosphate buffer, pH 8.0, 500 mM NaCl, 20 mM~1000 mM imidazole.

Dialyzate in step (4) is: 50 mM potassium phosphate buffer, pH 8.0, 500 mM NaCl.

Embodiment Twenty

The linear range of glycated albumin test kit

Including reagent 1 and reagent 2, wherein:

Reagent 1:

Tris hydrochloride buffer 50 mmol/L

Protease K40 KU/L

Peroxidase 30 KU/L 4-amino-antipyrine 10 mmol/L

Methyl-4-isothiazolin-3-one 0.02%

Reagent 2:

Tris hydrochloride buffer 50 mmol/L

Mutants of fructosyl amino acid oxidases 28 KU/L

N. N-bis(4-sulfobutyl)-3-methylaniline (TODB) 2 mmol/L

Methyl-4-isothiazolin-3-one 0.02%

The mutant of fructosyl amino acid oxidase used in the present embodiment particularly is No. M76 mutant. In fact, other mutants also can be used.

Fresh serum samples should be used for the test. The hemolysis should be avoided. After the serum is collected, if not promptly tested, it should be stored at 4 CC. Theoretically, it should not be stored for more than two weeks.

Detection conditions: Main wavelength of 600 nm, sub-wavelength of 700 nm.

Detection steps: shown in Table 21

TABLE 21

| Detection steps |
| --- |
| Sample 20 ul |
| Reagent 1 200 ul |
| mixing uniformly, incubating for 5 min at 37° C. |
| Reagent 2 50 ul |
| mixing uniformly, determining the absorbance value A1 within 20 s, incubating for 5 min at 37° C., determining the absorbance A2, calculating ΔA = A2 − A1 |

The linear range, shown in FIG. 1:

The serum having high GA value is taken, and is diluted into different gradients using normal saline, and will be measured respectively.

The linear range of glycated albumin detected by this method is 21.0~1200 umol/L, $r^2 > 0.990$.

Embodiment Twenty-one

Precision test of glycated albumin test kit

A high and low quality control and two serum samples are tested 20 times respectively. Mean values are 204 umol/L, 751 umol/L, 251 umol/L, 373 umol/L respectively. CVs are 1.1%, 0.7%, 0.8%, 0.6% respectively.

TABLE 22

| Intra-batch precision test | | | | |
| --- | --- | --- | --- | --- |
| | Quality control 1: 198 umol/L GA | Quality control 2: 750 umol/L GA | Serum 1: 241 umol/L GA | Serum 2: 375 umol/L GA |
| Testing times | 20 | 20 | 20 | 20 |
| Mean values | 204 | 751 | 251 | 373 |
| SD | 2.15 | 4.91 | 1.94 | 2.41 |
| CV % | 1.1 | 0.7 | 0.8 | 0.6 |

A high and low value quality control and two serum samples are continuously measured for 10 days respectively. Mean values are 204 umol/L, 751 umol/L, 251 umol/L, 373 umol/L, respectively. CVs are 1.2%, 0.7%, 1.3%, 1.0%, respectively.

TABLE 23

| Inter-batch precision test | | | | |
| --- | --- | --- | --- | --- |
| | Quality control 1: 198 umol/L GA | Quality control 2: 750 umol/L GA | Serum 1: 241 umol/L GA | Serum 2: 375 umol/L GA |
| Testing times | 20 | 20 | 20 | 20 |
| Mean values | 204 | 751 | 251 | 373 |
| SD | 2.39 | 9.59 | 5.18 | 6.75 |
| CV % | 1.2 | 1.3 | 2.1 | 1.8 |

Embodiment Twenty-two

Open-bottle stability test of glycated albumin test kit

On Hitachi biochemical analyzer, the open-bottle stability of the reagent can sustain for at least 4 weeks.

TABLE 24

| Open-bottle stability test | | | | | |
| --- | --- | --- | --- | --- | --- |
| GA | 0 days | 7 days | 14 days | 21 days | 28 days |
| Quality control 1: 198 umol/L GA | 203 | 202 | 206 | 202 | 206 |
| Quality control 2: 750 umol/L GA | 753 | 740 | 738 | 736 | 745 |
| N109657 270 umol/L | 274 | 271 | 274 | 269 | 272 |

Embodiment Twenty-three

Glycated albumin test kit and HPLC correlation

The glycated albumin detection test kit of the present invention and classical HPLC detection methods are used in the determination of the same sample, after comparison, it is found that the correlation is good, $R2 > 0.995$.

Embodiment Twenty-four

Anti-interference test of the glycated albumin test kit

It is found that, when the concentration of vitamin C is less than 0.2 mmol/L, hemoglobin less than 1.6 g/L, bilirubin less than 0.32 mmol/L, uncoupling bilirubin less than 0.32 mmol/L, triglyceride less than 20 mmol/L, blood glucose less than 20 g/L, uric acid less than 36 g/L, their interference of the measured value of glycated albumin is less than 10%.

TABLE 25

| Interference test | | |
| --- | --- | --- |
| Interferences | Interference concentration | Deviation |
| Vitamin C | 0.2 mmol/L | 2.1% |
| Hemoglobin | 1.6 g/L | 3.1% |
| Bilirubin | 0.32 mmol/L | −1.9% |
| Uncoupling bilirubin | 0.32 mmol/L | −2.8% |
| Triglyceride | 20 mmol/L | −6.6% |
| Blood glucose | 20 g/L | −1.5% |
| Uric acid | 36 g/L | 5.9% |

Embodiment Twenty-five

Determination of the percentage of glycated albumin

The detection of glycated albumin and the detection of albumin are combined, so as to obtain a percentage value of the glycated albumin through calculating the glycated albumin concentration divided by the albumin concentration.

The Albumin detection reagent is as follows

Reagent 3:

Succinate buffer 0.05 mol/L

Polyoxyethytene (23) lauryl ether 2.4 g/L

Bromocresol green $1.8 \times 10^{-4}$ mol/L

Test conditions: main wavelength of 600 nm, sub-wavelength of 700 nm.

Reaction method: end-point method.

Detection steps: shown in Table 26

TABLE 26

| Detection steps | |
| --- | --- |
| Sample | 3 ul |
| Reagent 3 | 300 ul | mixing uniformly, 37° C. incubating for 1 min, reading the absorbance A

Using the above method, 20 samples of serum are detected. The percentage of glycated albumin is calculated, as shown in Table 27.

TABLE 27

Percentages of glycated albumin of 20 samples of serum

| Sample number | Glycated albumin (umol/L) | Albumin (g/dL) | Percentage (Glycated albumin/Albumin) |
| --- | --- | --- | --- |
| 1 | 120 | 2.33 | 12.3% |
| 2 | 135 | 2.06 | 15.6% |
| 3 | 255 | 4.21 | 14.2% |
| 4 | 267 | 4.11 | 15.2% |
| 5 | 186 | 4.03 | 10.9% |
| 6 | 155 | 2.72 | 13.5% |
| 7 | 198 | 3.15 | 14.8% |
| 8 | 290 | 3.97 | 17.1% |
| 9 | 112 | 1.82 | 14.8% |
| 10 | 156 | 2.76 | 13.4% |
| 11 | 178 | 2.73 | 15.4% |
| 12 | 134 | 2.51 | 12.7% |
| 13 | 125 | 2.58 | 11.6% |
| 14 | 301 | 4.19 | 16.8% |
| 15 | 148 | 2.79 | 12.6% |
| 16 | 198 | 3.15 | 14.8% |
| 17 | 205 | 3.68 | 13.1% |
| 18 | 175 | 3.48 | 11.9% |
| 19 | 246 | 4.62 | 12.5% |
| 20 | 278 | 4.14 | 15.7% |

Typically, the reference value of glycated albumin is from 11% to 16%. An increased glycated albumin value is common in diabetes. The index can be used as a reference indicator of medium-term glucose control of diabetic patients.

Embodiment Twenty-six

Performance of glycated albumin test kit formulated using mutants of other fructosyl amino acid oxidases Since mutants of fructosyl amino acid oxidases involved in the present invention are so many, it is impossible to verify them in the glycated albumin test kit one by one. Therefore, only a few of the most typical mutants of fructosyl amino acid oxidases are selected for the glycated albumin detection test kit. Their performances are evaluated. Mutants of fructosyl amino acid oxidases involved in the present invention that are suitable for the glycated albumin test kits are used to illustrate the present invention, and cannot limit the present invention. The detection method of the involved test kit, verification methods of linear range, the intra-batch precision, the precision inter-batch, the open-bottle stability, the correlation with HPLC, the anti-interference, and etc. are the same as those of Embodiments twenty to twenty-five.

Glycated albumin test kit includes reagent 1 and reagent 2, wherein:

Reagent 1:

Tris hydrochloride buffer 50 mmol/L

Protease K 40 KU/L

Peroxidase 30 KU/L 4-amino-antipyrine 10 mmol/L

Methyl-4-isothiazolin-3-one 0.02%

Reagent 2:

Tris hydrochloride buffer 50 mmol/L

Fructosyl amino acid oxidase mutant 28 KU/L

N,N-bis(4-sulfobutyl)-3-methylaniline (TODB) 2 mmol/L

Methyl-4-isothiazolin-3-one 0.02%

In this embodiment, the following representatives are selected from mutant strains of fructosyl amino acid oxidases to be tested: i.e., those prepared in the above embodiments, M1, M13, M28, M35, M50, M56, M64, M73, M79, M80, M81, M90, M100, M109, and M120.

Performances of the above mutants of fructosyl amino acid oxidases and their corresponding glycated albumin test kit are shown in the table below in details.

TABLE 28

Performances of glycated albumin test kit prepared using different mutant strains of amino acid oxidase mutant fructose

| Sample number | Glycated albumin (umol/L) | Albumin (g/dL) | Percentage (Glycated albumin/Albumin) |
| --- | --- | --- | --- |
| 1 | 120 | 2.33 | 12.3% |
| 2 | 135 | 2.06 | 15.6% |
| 3 | 255 | 4.21 | 14.2% |
| 4 | 267 | 4.11 | 15.2% |
| 5 | 186 | 4.03 | 10.9% |
| 6 | 155 | 2.72 | 13.5% |
| 7 | 198 | 3.15 | 14.8% |
| 8 | 290 | 3.97 | 17.1% |
| 9 | 112 | 1.82 | 14.8% |
| 10 | 156 | 2.76 | 13.4% |
| 11 | 178 | 2.73 | 15.4% |
| 12 | 134 | 2.51 | 12.7% |
| 13 | 125 | 2.58 | 11.6% |
| 14 | 301 | 4.19 | 16.8% |
| 15 | 148 | 2.79 | 12.6% |
| 16 | 198 | 3.15 | 14.8% |
| 17 | 205 | 3.68 | 13.1% |
| 18 | 175 | 3.48 | 11.9% |
| 19 | 246 | 4.62 | 12.5% |
| 20 | 278 | 4.14 | 15.7% |

The above embodiments of the present invention are descriptions of the present invention, but not for limiting the present invention. Any change equivalent to the concept and scope of claims of the present invention should all be construed as falling within the scope of the claims.

What is claimed is:

1. A fructosyl amino acid oxidase comprising the amino acid sequence of SEQ ID No: 1, wherein glutamic acid at position 59 of SEQ ID No: 1 is substituted with an amino acid selected from the group consisting of L, I, V, F, M, W, T, C, N, Y, D, and H, and wherein the fructosyl amino acid exhibits a higher thermostability compared to the fructosyl amino acid oxidase of SEQ ID No: 1.

2. A fructosyl amino acid oxidase comprising the amino acid sequence of SEQ ID No: 1, wherein glutamic acid at position 59 of SEQ ID No: 1 is substituted with phenylalanine (F), wherein the fructosyl amino acid oxidase further comprises an additional substitution to SEQ ID No: 1 selected from the group consisting of substitutions (a) to (k), wherein the fructosyl amino acid exhibits a higher thermostability compared to the fructosyl amino acid oxidase of SEQ ID No: 1, and wherein the substitutions (a) to (k) are as follows:
  (a) E98C
  (b) G225D
  (c) K227N
  (d) E285F
  (e) E98C and G225F
  (f) G225D and K227N
  (g) K227N and E285I
  (h) E98C, G225F, and K277N
  (i) G225D, K277N, and E285F
  (j) E98C, G225F, K277N, and E285F
  (k) E98C, G225F, K227N, E285F, and D355L.

3. A polynucleotide encoding the fructosyl amino acid oxidase of claim 1.

4. A test kit for determining glycated albumin, the kit comprising a reagent 1 and reagent 2, wherein reagent 1 comprises 20-200 mM buffer, 10-100 KU/L protease, 10-100 KU/L peroxidase, 5-50 mM 4-amino-antipyrine, and 0.01 to 0.05% preservative, and wherein reagent 2 comprises 20-200 mM buffer, 10-100 KU/L of the fructosyl amino acid oxidase of claim 1, 1-10 mM chromogen, and 0.01 to 0.05% preservative.

5. The test kit of claim 4, wherein the buffer is selected from the group consisting of tris-hydrochloride buffer, acetic acid-sodium acetate buffer, phthalic-acid-hydrochloric acid buffer, and glycine-hydrochloric acid buffer.

6. The test kit of claim 4, wherein the protease is selected from the group consisting of trypsin, basophilic protease, proteinase A, and proteinase K.

7. The test kit of claim 4, wherein chromogen is selected from the group consisting of N, N-di(4-sulfobutyl)-3-methylaniline disodium salt, N-ethyl-N-(3-sulfopropyl)-3-methylaniline sodium salt, and N-ethyl-N-(2-hydroxy-3-sulfopropyl)-3-methylaniline sodium salt.

8. The test kit of claim 4, wherein the preservative is 2-methyl-4-isothiazolin-3-one.

* * * * *

SEQUENCE LISTING

<160> NUMBER OF SEQ ID NOS: 75

<210> SEQ ID NO 1
<211> LENGTH: 445
<212> TYPE: PRT
<213> ORGANISM: Aspergillus fumigatus

<400> SEQUENCE: 1

Met Ala Pro Ser Ile Leu Ser Thr Glu Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
            35                  40                  45

Ala Ala Gly Asn Asp Ile Asn Lys Ile Met Glu His Ser Glu Leu Lys
        50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Leu Pro Asp Pro Asn Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

```
Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
            435                 440                 445

<210> SEQ ID NO 2
<211> LENGTH: 1338
<212> TYPE: DNA
<213> ORGANISM: Aspergillus fumigatus

<400> SEQUENCE: 2
atggcgcctt caattttgag cactgaatct tccattatcg ttatcggagc aggcacatgg      60
ggctgctcaa ctgctctgca cctcgctcgt cgaggctaca agatgtcac tgttctcgac     120 cctcatccag ttccttcgcc cattgcagca ggcaatgaca tcaacaagat tatggagcac     180
agcgagctga agatggctc atccgaccct cgaagcgcag ccttctcgac atttacgcga     240
gctgctctta aggcgtggaa aactgacccg gttttccagc cttactttca cgaaactggc     300
tttatcatat cggggcacac acctgctctg attgaccaca tacgaaaaga cgaggtagaa     360
ccgtcagaaa caaacttcgt caagctggag acagccgagg acttccgccg gaccatgccg     420
ccaggtgtac tgacaggcga cttccctggc tggaaaggct ggttgcacaa gtctggtgct     480
gggtggattc atgccaaaaa ggctatgatc tctgctttca tgaagctaa gcgcttggga     540 gtcagatttg tcactggctc tccggaaggg aatgttgtat cgttggtata cgaggacgga     600
gacgtcgttg gagccagaac tgccgatggt cgcgtgcaca agcccatcg cactattctt     660 tcggcaggtg ctggcagtga cagtctccta gacttcaaga gcagcttcg gcctaccgcg     720 tggactctct gtcatattca gatgggcccct gaagaggtca gcaatatcg gaaccttcct     780 gtgttgttca acatcgccaa agggttcttc atggagcctg atgaggataa cacgagctc     840 aagatttgtg acgagcatcc agggtactgc aactttctcc ctgacccaaa cagaccgggc     900
caggagaaga gtgtccccctt cgcaaagcat cagatcccgc tcgaggccga agcccgcgca     960
cgagactttc tccatgatac aatgccgcat ctggctgacc ggccactgtc tttcgcgcgt    1020
atttgctggg atgctgatac cccagaccgt gctttcttga tcgatagaca tcctgaacac    1080
ccctcactgc tagtcgctgt tggaggttcc ggcaatggcg ccatgcaaat gcctacaatt    1140
ggcggtttta tcgcagatgc tctagagagt aaactacaga aggaggtgaa ggacatcgtt    1200
cgatggaggc cagagacggc tgtcgatcga gattggagag cgactcagaa tcgctttggc    1260
gggcctgaca ggatcatgga ttttcagcag gtcggagagg atcagtggac caagattgga    1320
gagagcagag gtccgtaa                                                   1338

<210> SEQ ID NO 3
<211> LENGTH: 25
<212> TYPE: DNA
<213> ORGANISM: Artificial Sequence
<220> FEATURE:
<223> OTHER INFORMATION: Synthetic
```

-continued

```
<400> SEQUENCE: 3
atggcgcctt caattttgag cactg                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ttacggacct ctgctctctc caatc                                          25

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tgctagttat tgctcagcgg                                                20

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
aacaagatta tgttacacag cgagctg                                        27

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
aacaagatta tgattcacag cgagctg                                        27

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
aacaagatta tggtgcacag cgagctg                                        27

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
aacaagatta tgtttcacag cgagctg                                        27

<210> SEQ ID NO 10
<211> LENGTH: 27
```

```
<212> TYPE: DNA
<213> ORGANISM: Artificial Sequence
<220> FEATURE:
<223> OTHER INFORMATION: Synthetic

<400> SEQUENCE: 10
aacaagatta tgatgcacag cgagctg                                              27

<210> SEQ ID NO 11
<211> LENGTH: 27
<212> TYPE: DNA
<213> ORGANISM: Artificial Sequence
<220> FEATURE:
<223> OTHER INFORMATION: Synthetic

<400> SEQUENCE: 11
aacaagatta tgtggcacag cgagctg                                              27

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
aacaagatta tgactcacag cgagctg                                              27

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
aacaagatta tgtgtcacag cgagctg                                              27

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14
aacaagatta tgaatcacag cgagctg                                              27

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
aacaagatta tgtatcacag cgagctg                                              27

<210> SEQ ID NO 16
<211> LENGTH: 27
<212> TYPE: DNA
<213> ORGANISM: Artificial Sequence
<220> FEATURE:
<223> OTHER INFORMATION: Synthetic

<400> SEQUENCE: 16
```
aacaagatta tggatcacag cgagctg          27

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
aacaagatta tgcaccacag cgagctg          27

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
ccttactttc acgcgactgg ctttatc          27

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
ccttactttc acttaactgg ctttatc          27

<210> SEQ ID NO 20
<211> LENGTH: 27
<212> TYPE: DNA
<213> ORGANISM: Artificial Sequence
<220> FEATURE:
<223> OTHER INFORMATION: Synthetic

<400> SEQUENCE: 20
ccttactttc acattactgg ctttatc          27

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
ccttactttc acgtgactgg ctttatc          27

<210> SEQ ID NO 22
<211> LENGTH: 27
<212> TYPE: DNA
<213> ORGANISM: Artificial Sequence
<220> FEATURE:
<223> OTHER INFORMATION: Synthetic

<400> SEQUENCE: 22
ccttactttc accccactgg ctttatc          27

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
ccttactttc actttactgg ctttatc        27

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
ccttactttc acagtactgg ctttatc        27

<210> SEQ ID NO 25
<211> LENGTH: 27
<212> TYPE: DNA
<213> ORGANISM: Artificial Sequence
<220> FEATURE:
<223> OTHER INFORMATION: Synthetic

<400> SEQUENCE: 25
ccttactttc acactactgg ctttatc        27

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
ccttactttc actgtactgg ctttatc        27

<210> SEQ ID NO 27
<211> LENGTH: 27
<212> TYPE: DNA
<213> ORGANISM: Artificial Sequence
<220> FEATURE:
<223> OTHER INFORMATION: Synthetic

<400> SEQUENCE: 27
ccttactttc acaatactgg ctttatc        27

<210> SEQ ID NO 28
<211> LENGTH: 27
<212> TYPE: DNA
<213> ORGANISM: Artificial Sequence
<220> FEATURE:
<223> OTHER INFORMATION: Synthetic

<400> SEQUENCE: 28
ccttactttc actatactgg ctttatc        27

<210> SEQ ID NO 29
<211> LENGTH: 27
<212> TYPE: DNA
<213> ORGANISM: Artificial Sequence
<220> FEATURE:
<223> OTHER INFORMATION: Synthetic

<400> SEQUENCE: 29
ccttactttc acgatactgg ctttatc        27

```
<210> SEQ ID NO 30
<211> LENGTH: 27
<212> TYPE: DNA
<213> ORGANISM: Artificial Sequence
<220> FEATURE:
<223> OTHER INFORMATION: Synthetic

<400> SEQUENCE: 30
ccttactttc accacactgg ctttatc                                              27

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
tcggcaggtg ctgcgagtga cagtctc                                              27

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
tcggcaggtg ctttaagtga cagtctc                                              27

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
tcggcaggtg cttttagtga cagtctc                                              27

<210> SEQ ID NO 34
<211> LENGTH: 27
<212> TYPE: DNA
<213> ORGANISM: Artificial Sequence
<220> FEATURE:
<223> OTHER INFORMATION: Synthetic

<400> SEQUENCE: 34
tcggcaggtg ctatgagtga cagtctc                                              27

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
tcggcaggtg cttggagtga cagtctc                                              27

<210> SEQ ID NO 36
<211> LENGTH: 27
<212> TYPE: DNA
<213> ORGANISM: Artificial Sequence
<220> FEATURE:
<223> OTHER INFORMATION: Synthetic
```

-continued

<400> SEQUENCE: 36
tcggcaggtg ctagtagtga cagtctc					27

<210> SEQ ID NO 37
<211> LENGTH: 27
<212> TYPE: DNA
<213> ORGANISM: Artificial Sequence
<220> FEATURE:
<223> OTHER INFORMATION: Synthetic

<400> SEQUENCE: 37
tcggcaggtg ctaatagtga cagtctc					27

<210> SEQ ID NO 38
<211> LENGTH: 27
<212> TYPE: DNA
<213> ORGANISM: Artificial Sequence
<220> FEATURE:
<223> OTHER INFORMATION: Synthetic

<400> SEQUENCE: 38
tcggcaggtg ctgatagtga cagtctc					27

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
cctgatgagg atgcgcacga gctcaag					27

<210> SEQ ID NO 40
<211> LENGTH: 27
<212> TYPE: DNA
<213> ORGANISM: Artificial Sequence
<220> FEATURE:
<223> OTHER INFORMATION: Synthetic

<400> SEQUENCE: 40
cctgatgagg atttacacga gctcaag					27

<210> SEQ ID NO 41
<211> LENGTH: 27
<212> TYPE: DNA
<213> ORGANISM: Artificial Sequence
<220> FEATURE:
<223> OTHER INFORMATION: Synthetic

<400> SEQUENCE: 41
cctgatgagg atattcacga gctcaag					27

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
cctgatgagg attttcacga gctcaag					27

<210> SEQ ID NO 43

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
cctgatgagg atagtcacga gctcaag                                        27

<210> SEQ ID NO 44
<211> LENGTH: 27
<212> TYPE: DNA
<213> ORGANISM: Artificial Sequence
<220> FEATURE:
<223> OTHER INFORMATION: Synthetic

<400> SEQUENCE: 44
cctgatgagg atactcacga gctcaag                                        27

<210> SEQ ID NO 45
<211> LENGTH: 27
<212> TYPE: DNA
<213> ORGANISM: Artificial Sequence
<220> FEATURE:
<223> OTHER INFORMATION: Synthetic

<400> SEQUENCE: 45
cctgatgagg ataatcacga gctcaag                                        27

<210> SEQ ID NO 46
<211> LENGTH: 27
<212> TYPE: DNA
<213> ORGANISM: Artificial Sequence
<220> FEATURE:
<223> OTHER INFORMATION: Synthetic

<400> SEQUENCE: 46
cctgatgagg attatcacga gctcaag                                        27

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cctgatgagg atagacacga gctcaag                                        27

<210> SEQ ID NO 48
<211> LENGTH: 27
<212> TYPE: DNA
<213> ORGANISM: Artificial Sequence
<220> FEATURE:
<223> OTHER INFORMATION: Synthetic

<400> SEQUENCE: 48
cctgatgagg atcaccacga gctcaag                                        27

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
aagatttgtg acgcgcatcc agggtac                                              27

<210> SEQ ID NO 50
<211> LENGTH: 27
<212> TYPE: DNA
<213> ORGANISM: Artificial Sequence
<220> FEATURE:
<223> OTHER INFORMATION: Synthetic

<400> SEQUENCE: 50
aagatttgtg acttacatcc agggtac                                              27

<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
aagatttgtg acattcatcc agggtac                                              27

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
aagatttgtg actttcatcc agggtac                                              27

<210> SEQ ID NO 53
<211> LENGTH: 27
<212> TYPE: DNA
<213> ORGANISM: Artificial Sequence
<220> FEATURE:
<223> OTHER INFORMATION: Synthetic

<400> SEQUENCE: 53
aagatttgtg acatgcatcc agggtac                                              27

<210> SEQ ID NO 54
<211> LENGTH: 27
<212> TYPE: DNA
<213> ORGANISM: Artificial Sequence
<220> FEATURE:
<223> OTHER INFORMATION: Synthetic

<400> SEQUENCE: 54
aagatttgtg actggcatcc agggtac                                              27

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
aagatttgtg accaacatcc agggtac                                              27

<210> SEQ ID NO 56
<211> LENGTH: 27
<212> TYPE: DNA

```
<213> ORGANISM: Artificial Sequence
<220> FEATURE:
<223> OTHER INFORMATION: Synthetic

<400> SEQUENCE: 56
aagatttgtg acaatcatcc agggtac                                              27

<210> SEQ ID NO 57
<211> LENGTH: 27
<212> TYPE: DNA
<213> ORGANISM: Artificial Sequence
<220> FEATURE:
<223> OTHER INFORMATION: Synthetic

<400> SEQUENCE: 57
gctttcttga tcttaagaca tcctgaa                                              27

<210> SEQ ID NO 58
<211> LENGTH: 27
<212> TYPE: DNA
<213> ORGANISM: Artificial Sequence
<220> FEATURE:
<223> OTHER INFORMATION: Synthetic

<400> SEQUENCE: 58
gctttcttga tcattagaca tcctgaa                                              27

<210> SEQ ID NO 59
<211> LENGTH: 27
<212> TYPE: DNA
<213> ORGANISM: Artificial Sequence
<220> FEATURE:
<223> OTHER INFORMATION: Synthetic

<400> SEQUENCE: 59
gctttcttga tcgtgagaca tcctgaa                                              27

<210> SEQ ID NO 60
<211> LENGTH: 27
<212> TYPE: DNA
<213> ORGANISM: Artificial Sequence
<220> FEATURE:
<223> OTHER INFORMATION: Synthetic

<400> SEQUENCE: 60
gctttcttga tctttagaca tcctgaa                                              27

<210> SEQ ID NO 61
<211> LENGTH: 27
<212> TYPE: DNA
<213> ORGANISM: Artificial Sequence
<220> FEATURE:
<223> OTHER INFORMATION: Synthetic

<400> SEQUENCE: 61
gctttcttga tcatgagaca tcctgaa                                              27

<210> SEQ ID NO 62
<211> LENGTH: 27
<212> TYPE: DNA
<213> ORGANISM: Artificial Sequence
<220> FEATURE:
<223> OTHER INFORMATION: Synthetic

<400> SEQUENCE: 62
gctttcttga tctggagaca tcctgaa                                              27
```

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
gctttcttga tcactagaca tcctgaa                                                27

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
gctttcttga tctgtagaca tcctgaa                                                27

<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65
gctttcttga tctatagaca tcctgaa                                                27

<210> SEQ ID NO 66
<211> LENGTH: 27
<212> TYPE: DNA
<213> ORGANISM: Artificial Sequence
<220> FEATURE:
<223> OTHER INFORMATION: Synthetic

<400> SEQUENCE: 66
gctttcttga tcagaagaca tcctgaa                                                27

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
gctttcttga tccacagaca tcctgaa                                                27

<210> SEQ ID NO 68
<211> LENGTH: 443
<212> TYPE: PRT
<213> ORGANISM: Aspergillus niger CBS 513.88

<400> SEQUENCE: 68

Met Ala Pro Ser Thr Val Thr His Asp Ser Thr Ile Leu Val Val Gly
1               5                   10                  15

Ala Gly Val Trp Gly Cys Ser Thr Ala Leu His Leu Ala Arg Arg Gly
                20                  25                  30

Tyr Lys His Val Thr Val Leu Asp Pro Tyr Thr Val Pro Ser Ala Ile
            35                  40                  45

Ala Ala Gly Asn Asp Ile Asn Lys Ile Met Glu His Lys Glu Pro Lys

```
                50                  55                  60
Ala Gly Glu Glu Ser Pro Arg Ser Ile Ala Phe Ala Thr Cys Thr Arg
 65                  70                  75                  80

Ala Ala Leu Lys Ala Trp Arg Thr Asp Pro Val Phe Lys Gln Tyr Phe
                 85                  90                  95

His Glu Thr Gly Val Ile Val Ser Gly His Thr Pro Ala Leu Ile Glu
                100                 105                 110

His Ile Arg Lys Asp Glu Ile Glu Ser Ser Asp Ala Asp Phe Val Glu
                115                 120                 125

Leu Lys Thr Ala Glu Asp Phe Arg Lys Thr Met Pro Pro Gly Val Leu
130                 135                 140

Thr Gly Glu Phe Pro Gly Trp Lys Gly Trp Leu Asn Lys Ser Gly Ala
145                 150                 155                 160

Gly Trp Ile His Ala Lys Lys Ala Met Ile Ser Ala Tyr Thr Glu Ala
                165                 170                 175

Lys Arg Leu Gly Val Asn Phe Ile Thr Gly Ser Pro Gln Gly Asn Val
                180                 185                 190

Val Ser Leu Val Tyr Glu Asn Gly Asp Val Val Gly Ala Lys Thr Ser
                195                 200                 205

Asp Gly Val Ile His Arg Ala Asp Gln Thr Ile Leu Ala Ala Gly Ala
210                 215                 220

Gly Ser Asp Arg Leu Leu Asp Phe Lys Lys Gln Leu Arg Pro Thr Ala
225                 230                 235                 240

Trp Thr Leu Ser His Ile Gln Met Thr Pro Glu Glu Ala Lys Gln Tyr
                245                 250                 255

Lys Asp Leu Pro Val Leu Phe Asn Ile Ala Lys Gly Phe Phe Met Glu
                260                 265                 270

Pro Asp Glu Asp Lys His Glu Leu Lys Ile Cys Asp Glu His Pro Gly
                275                 280                 285

Tyr Cys Asn Phe Ile Pro Asp Pro Ala Arg Ser Gly Glu Ile Arg Ser
                290                 295                 300

Ile Pro Phe Ala Lys His Gln Ile Pro Leu Glu Ala Glu Ala Arg Val
305                 310                 315                 320

Lys Asp Phe Leu Arg Asp Thr Met Pro His Leu Ala Asp Arg Pro Leu
                325                 330                 335

Val Phe Ala Arg Ile Cys Trp Asp Ala Asp Thr Val Ser Arg Ala Phe
                340                 345                 350

Leu Ile Asp Lys His Pro Asp His Pro Ser Leu Leu Val Ala Val Gly
                355                 360                 365

Ala Ser Gly Asn Gly Ala Met Gln Met Pro Thr Ile Gly Gly Phe Ile
370                 375                 380

Val Asp Ala Leu Glu Gly His Leu Gln Asp Glu Leu Lys His Val Val
385                 390                 395                 400

Arg Trp Arg Pro Glu Thr Ala Val Asp Arg Asp Trp Lys Ser Thr Gln
                405                 410                 415

Asn Arg Phe Gly Gly Pro Asp Ala Val Met Asp Phe Gln Thr Val Gly
                420                 425                 430

Glu Thr Glu Trp Thr Lys Ile Lys Ser Arg Leu
                435                 440

<210> SEQ ID NO 69
<211> LENGTH: 1332
<212> TYPE: DNA
<213> ORGANISM: Aspergillus niger CBS 513.88
```

<400> SEQUENCE: 69

```
atggcaccct ccacggtaac ccatgattct accatcctcg tggtgggagc gggtgtatgg      60
ggttgttcta ctgctttgca tttggctcgt cgcggatata agcatgtcac ggttctagac     120
ccctacacgg tcccatccgc aatcgcagcc ggcaatgata tcaacaagat catggaacac     180
aaggagccca agcaggcga agaaagtcca cgcagcattg cgttcgcgac gtgcactcgt     240
gccgctctga agcgtggcg acgatcct gttttcaagc agtactttca tgagaccggt     300
gtcatagtat ccggtcatac cccggcactc attgagcaca tccgcaaaga cgaaatcgag     360
tcatctgatg cagactttgt cgaattgaag acagcagaag acttccgaaa gacaatgcct     420
ccaggtgttc tcactggtga gtttcctggc tggaagggct ggttgaacaa gtcgggtgcc     480
ggctggattc atgccaagaa agccatgatc tctgcgtaca ctgaagccaa gcgtcttggg     540
gtcaacttca tcactggatc tccccagggg aacgttgtat cactagtata cgagaatgga     600
gatgtggttg gagctaaaac gtccgatggg gtcattcatc gagcagacca aaccattttg     660
gcagccggtg cgggaagtga ccgtctcctg gatttcaaga aacagctgcg tcctactgcc     720
tggacgctct ctcatattca gatgacccct gaggaggcca agcagtacaa ggattaccc     780
gtgcttttca atattgcgaa ggggttcttc atggagcctg atgaggataa gcacgaactg     840
aagatcgtg acgagcatcc tggatactgt aactttattc cagaccctgc aagatccggc     900
gagatcagaa gcatcccatt tgcgaagcat caaattcccc tggaggccga agctcgcgtt     960
aaggacttcc tgcgggatac aatgccacac ttggccgacc gtccgctggt atttgcccgt    1020
atctgctggg atgctgacac ggtagatcgc gccttttga tcgataaaca tcctgaccac    1080
ccttcactgc tggtcgccgt gggagcttct gggaacgggg ctatgcagat gcccactatt    1140
ggagggttca ttgtggatgc actggagggt cacctacaag atgagctaaa acatgtcgtt    1200
cggtggaggc cagaaacagc ggtcgacaga gactggaagt cgacacgaa ccgtttcgga    1260
ggaccagatg cggttatgga cttccagacg gttggcgaaa ctgaatggac caagatcaag    1320
agccggctat ag                                                      1332
```

<210> SEQ ID NO 70
<211> LENGTH: 441
<212> TYPE: PRT
<213> ORGANISM: Aspergillus clavatus NRRL 1

<400> SEQUENCE: 70

```
Met Ala Pro Ser Pro Leu Ser Ile Glu Ser Ser Ile Leu Ile Ile Gly
1               5                   10                  15

Ala Gly Thr Trp Gly Cys Ser Thr Ala Leu Asp Ile Ala Arg Arg Gly
            20                  25                  30

Tyr Lys His Val Thr Val Leu Asp Pro His Pro Val Pro Ser Pro Ile
        35                  40                  45

Ala Ala Gly Asn Asp Ile Asn Lys Ile Met Glu His Asn Glu Leu Lys
    50                  55                  60

Asp Gly Glu Pro Asp Ser Arg Ser Ile Ala Phe Ala Thr Phe Thr Arg
65                  70                  75                  80

Ala Ala Leu Asn Ala Trp Lys Thr Asp Pro Val Phe Gln Pro Phe Phe
                85                  90                  95

His Glu Thr Gly Ala Ile Val Ser Gly His Thr Pro Ala Leu Leu Lys
            100                 105                 110

His Ile Gln Glu Asp Glu Ile Asp Pro Ser Glu Thr Ala Phe Val Gln
```

115                 120                 125
Leu Glu Thr Ala Glu Asp Phe Arg Gly Thr Met Pro Ala Gly Val Leu
        130                 135                 140

Thr Gly Asp Phe Pro Gly Trp Lys Gly Trp Trp Arg Lys Asp Gly Ala
145                 150                 155                 160

Gly Trp Ile His Ala Lys Lys Ala Met Val Ser Ala Phe Ser Glu Ala
                165                 170                 175

Arg Arg Leu Gly Val Thr Phe Val Thr Gly Ser Pro Glu Gly Asn Val
            180                 185                 190

Asp Ser Leu Ala Tyr Glu Gly Gly Asp Val Ile Gly Ala Arg Thr Ala
        195                 200                 205

Asp Gly Lys Leu His Arg Ala Asp Tyr Thr Ile Leu Ser Ala Gly Ala
        210                 215                 220

Gly Ser Asp Met Leu Leu Asp Phe Lys Lys Gln Leu Arg Pro Thr Ala
225                 230                 235                 240

Trp Thr Leu Cys His Ile Gln Met Thr Pro Glu Glu Ala Ala Arg Tyr
                245                 250                 255

Arg Asn Leu Pro Val Leu Phe Asn Ile Ala Lys Gly Phe Phe Met Glu
            260                 265                 270

Pro Asp Ala Asp Asn His Glu Leu Lys Ile Cys Asp Glu His Pro Gly
        275                 280                 285

Tyr Cys Asn Phe Leu Pro Asp Pro Asp Arg Pro Gly Glu Thr Arg Ser
        290                 295                 300

Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Glu Arg Pro Leu
                325                 330                 335

Ser Phe Ala Arg Ile Cys Trp Asp Ala Asp Thr Pro Arg Ala Phe
            340                 345                 350

Leu Ile Asp Lys His Pro Glu Tyr Pro Ser Leu Val Val Ala Val Gly
        355                 360                 365

Gly Ser Gly Asn Gly Ala Met Gln Met Pro Thr Ile Gly Gly Phe Ile
        370                 375                 380

Ala Asp Ala Leu Glu Gly Ser Leu Gln Lys Asp Leu Lys Asp Val Val
385                 390                 395                 400

Arg Trp Arg Pro Glu Thr Ala Val Gly Arg Asp Trp Arg Ala Thr Gln
                405                 410                 415

Asn Arg Phe Gly Gly Pro Gly Gln Ile Met Asp Phe Gln Asn Leu Glu
            420                 425                 430

Glu Gly Gln Trp Thr Arg Ile Lys Val
        435                 440

<210> SEQ ID NO 71
<211> LENGTH: 1326
<212> TYPE: DNA
<213> ORGANISM: Aspergillus clavatus NRRL 1

<400> SEQUENCE: 71
atggcgcctt caccattgag catcgaatcc tccatcttga ttatcggagc tggaacttgg      60
ggctgctcga ctgctctgga tattgctcgt cgaggataca agcatgtcac tgtcctggat     120
cctcatccgg ttccttcgcc catcgcggca ggcaatgata tcaacaagat tatggaacac     180
aatgagctca agatgggga gccggattcc cggagtatcg ccttcgcaac gttcacgcga     240
gctgctctga acgcgtggaa gacagacccc gtcttccaac cgttcttcca tgaaactggt     300

```
gcaatcgtat caggccacac gcctgcttta ctcaagcaca tacaggaaga cgaaatcgat    360
ccttccgaga ccgcattcgt ccaacttgag actgcagagg actttcgcgg cacgatgccc    420
gccggggtgc tcactggcga cttcccaggc tggaaaggat ggtggcgcaa ggatggtgct    480
ggctggatcc acgccaaaaa ggccatggtc tctgcattca gtgaggctag gcggctaggc    540
gttactttcg tcactggctc tccggagggg aatgtcgatt ccctagccta tgagggcggc    600
gatgtaatcg gagccaggac tgcagatggc aaactgcaca gagccgacta caccatcctg    660
tcagcaggcg ctggaagcga catgctcctg gatttcaaga agcagcttcg tcccaccgcc    720
tggacgctct gccatatcca gatgaccccg gaagaggccg cgcggtaccg gaacctccct    780
gttctgttta acatcgccaa gggcttcttc atggagccag atgcggataa ccacgagctc    840
aagatctgcg acgagcatcc gggctactgc aacttcctcc ccgacccaga ccggccaggc    900
gagacgagga gtatcccatt cgccaagcac cagattccgc tggaggccga agctcgagcg    960
agagactttc tccgcgatac gatgcctcat ctggctgagc ggcccttgtc ttttgcccgg   1020
atatgctggg acgcggacac cccggaccgg gcgttcttga tcgataaaca cccggagtat   1080
ccttccttgg tggttgccgt aggaggctcg gggaatggtg cgatgcagat gcccactatt   1140
ggcggcttta tcgccgacgc actggaaggg agtttgcaga aagatttgaa ggatgttgta   1200
cgctggagac cggagacggc ggttggtcga cactggaggg caacgcagaa tcgctttggg   1260
ggacccggac agattatgga ttttcaaaac cttgagagg gacaatggac caggatcaag   1320
gtgtag                                                               1326
```

<210> SEQ ID NO 72
<211> LENGTH: 446
<212> TYPE: PRT
<213> ORGANISM: Neosartorya fischeri NRRL 181

<400> SEQUENCE: 72

```
Met Ala Pro Ser Asn Leu Thr Thr Glu Ser Ser Ile Leu Ile Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Ile Phe Gln Pro Tyr Phe
                85                  90                  95

His Glu Thr Gly Phe Ile Ile Ser Gly His Thr Pro Ala Leu Ile Glu
            100                 105                 110

His Ile Arg Lys Asp Glu Val Glu Pro Ser Gly Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp His Lys Ser Gly Ala
145                 150                 155                 160

Gly Trp Val His Ala Lys Lys Ala Met Ile Ser Ala Phe Asn Glu Ala
                165                 170                 175

Lys Arg Leu Gly Val Lys Phe Val Thr Ser Ser Pro Glu Gly Asn Val
```

```
                180                 185                 190
Val Ser Leu Val Tyr Glu Asp Gly Asp Val Val Gly Ala Lys Thr Ala
        195                 200                 205

Asp Gly Arg Val His Arg Ala His Arg Thr Ile Leu Ser Ala Gly Ala
        210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Asp Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Leu Ser Asp Pro Asp Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu Arg Asp Thr Met Pro His Leu Ala Gly Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

Gly Ser Gly Asn Gly Ala Met Gln Ile Pro Thr Ile Gly Gly Phe Ile
    370                 375                 380

Ala Asp Ala Leu Glu Ser Lys Leu Gln Lys Glu Val Lys Asp Val Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Gln Leu
        435                 440                 445

<210> SEQ ID NO 73
<211> LENGTH: 1341
<212> TYPE: DNA
<213> ORGANISM: Neosartorya fischeri NRRL 181

<400> SEQUENCE: 73
atggcgcctt caaacttgac cactgaatct tccatcctca ttatcggagc aggcacatgg      60
ggctgctcaa ctgctctaca tctcgctcgt cgaggctaca agatgtgac agttctcgac     120 cctcatccag ttccttcgcc catcgcagca ggcaatgaca tcaacaagat tatggagcac     180
agcgagctca aggatggctc atccgacccc agaagcgcag ccttctcgac attcacgcga     240
gctgctctaa agcctggaa aactgacccg atttccagc cttactttca cgaaactggc      300
tttatcatat cggggcacac acctgctctg attgagcaca tacgaaaaga cgaggtagaa     360
ccgtcagaaa caacttcgt caagctggag acagccgagg acttccgccg gaccatgccg      420
ccgggcgtac tgacaggcga cttccctggc tggaaaggct ggtggcacaa gtctggtgct     480
gggtgggttc atgccaagaa ggctatgatc tctgctttca atgaagctaa gcgcttggga     540
gtcaaattcg tcactagctc tccggaagga aatgtcgtat cgttagtata cgaggatgga     600
gatgtcgttg gagctaaaac tgccgatggt cgcgtacaca gagcccatcg cactattctt     660
```

```
tcggcaggtg ctggcagtga cagtctccta gacttcaaga agcagcttcg gcctaccgcg    720
tggactctct gtcacattca gatggaccca gaagaggtca agcaataccg gaaccttccc    780
gtgctgttca acatcgccaa aggcttcttc atggagcctg atgaggataa acacgagctc    840
aagatttgtg acgaacatcc agggtactgc aactttctct ctgacccaga cagaccgggc    900
caggagaaga gtgtccccct tcgcaaagca tcagatcccg ctcgaggccga agcccgcgca    960
cgagactttc tccgtgatac aatgccgcat ctggctggcc ggccactgtc tttcgcgcgc   1020
atttgctggg atgctgatac cccggaccgt gctttcttga tcgatagaca tcctgaacac   1080
ccctcactgc tagtcgcagt tggaggttcc ggcaatggcg ccatgcaaat tcctacaatc   1140
ggcggcttta tcgcagatgc tctagaaagt aaactacaga aggaggtgaa ggacgtcgtt   1200
cgatggaggc cggagacggc tgtcgaccga gactggagag caactcagaa tcgcttcggc   1260
gggcctgaca ggatcatgga ttttcagcaa gtcggagagg atcagtggac caagattgga   1320
gagagcagag gtcagttata g                                              1341
```

<210> SEQ ID NO 74
<211> LENGTH: 445
<212> TYPE: PRT
<213> ORGANISM: Aspergillus fumigatus Af293

<400> SEQUENCE: 74

```
Met Ala Pro Ser Ile Leu Ser Thr Glu Ser Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255
```

Arg Asn Leu Pro Val Leu Phe Asn Ile Ala Lys Gly Phe Phe Ile Glu
            260                 265                 270

Pro Asp Glu Asp Lys Leu Glu Leu Lys Ile Cys Asp Glu His Pro Gly
        275                 280                 285

Tyr Cys Asn Phe Leu Pro Asp Pro Asn Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Ser Arg Ala Phe
            340                 345                 350

Leu Ile Asp Arg His Pro Glu His Pro Ser Leu Leu Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
        435                 440                 445

<210> SEQ ID NO 75
<211> LENGTH: 1338
<212> TYPE: DNA
<213> ORGANISM: Aspergillus fumigatus Af293

<400> SEQUENCE: 75
atggcgcctt caattttgag cactgaatct tccattatcg ttatcggagc aggcacatgg      60
ggctgctcaa ctgctctgca tctcgctcgt cgaggctaca agatgtcac tgttctcgac      120 cctcatccag ttccttcgcc cattgcagca ggcaatgaca tcaacaagat tatggagcac      180
agcgagctga agatggctc atccgaccct cgaagcgcag ccttctcgac atttacgcga      240
gctgctctta aggcgtggaa aactgacccg gttttccagc cttactttca cgaaactggc      300
tttatcatat cggggcacac acctgctctg attgaccaca tacgaaaaga cgaggtagaa      360
ccgtcagaaa caaacttcgt caagctggag acagccgagg acttccgccg gaccatgccg      420
ccaggtgtac tgacaggcga cttccctggc tggaaaggct ggttgcacaa gtctggtgct      480
gggtggattc atgccaaaaa ggctatgatc tctgctttca atgaagctaa gcgcttggga      540
gtcagatttg tcactggctc tccggaaggg aatgttgtat cgttggtata cgaggacgga      600
gacgtcgttg gagccagaac tgccgatggt cgcgtgcaca agcccatcg cactattctt      660 tcggcaggtg ctggcagtga cagtctccta gacttcaaga agcagcttcg gcctaccgcg      720
tggactctct gtcatattca gatgggccct gaagaggtca gcaatatcg gaaccttcct      780 gtgttgttca acatcgccaa agggttcttc attgagcctg atgaggataa actcgagctc      840
aagatttgtg acgagcatcc agggtactgc aactttctcc ctgacccaaa cagaccgggc      900
caggagaaga gtgtcccctt cgcaaagcat cagatcccgc tcgaggccga agccgcgca      960 cgagactttc tccatgatac aatgccgcat ctggctgaca ggccactgtc tttcgcgcgt      1020
atttgctggg atgctgatac cccagaccgt gctttcttga tcgatagaca tcctgaacac      1080

```
ccctcactgc tagtcgctgt tggaggttcc ggcaatggcg ccatgcaaat gcctacaatt     1140
ggcggtttta tcgcagatgc tctagagagt aaactacaga aggaggtgaa ggacatcgtt     1200
cgatggaggc cagagacggc tgtcgatcga gattggagag cgactcagaa tcgctttggc     1260
gggcctgaca ggatcatgga ttttcagcag gtcggagagg atcagtggac caagattgga     1320
gagagcagag gtccgtaa                                                   1338
```